(12) United States Patent
Tour et al.

(10) Patent No.: US 8,440,467 B2
(45) Date of Patent: May 14, 2013

(54) ELECTRONIC SWITCHING, MEMORY, AND SENSOR DEVICES FROM A DISCONTINUOUS GRAPHENE AND/OR GRAPHITE CARBON LAYER ON DIELECTRIC MATERIALS

(75) Inventors: James M. Tour, Bellaire, TX (US); Yubao Li, Houston, TX (US); Alexander Sinitskiy, Ryazan (RU)

(73) Assignee: William Marsh Rice University, Houston, TX (US)

( * ) Notice: Subject to any disclaimer, the term of this patent is extended or adjusted under 35 U.S.C. 154(b) by 565 days.

(21) Appl. No.: 12/240,673

(22) Filed: Sep. 29, 2008

(65) Prior Publication Data
US 2010/0279426 A1    Nov. 4, 2010

Related U.S. Application Data

(60) Provisional application No. 60/976,143, filed on Sep. 28, 2007.

(51) Int. Cl.
   *G01N 27/06*    (2006.01)
(52) U.S. Cl.
   USPC ............ 436/149; 422/82.01; 422/82.02; 422/88; 422/90; 422/98; 436/150; 436/151
(58) Field of Classification Search .... 422/82.01–82.02, 422/88, 90, 98; 436/149–151
   See application file for complete search history.

(56) References Cited

U.S. PATENT DOCUMENTS

| | | | | |
|---|---|---|---|---|
| 4,890,186 A * | 12/1989 | Matsubara et al. | ........... | 361/103 |
| 5,075,738 A * | 12/1991 | Matsuda et al. | ................ | 257/49 |
| 5,153,753 A | 10/1992 | Ohta et al. | | |
| 5,250,451 A * | 10/1993 | Chouan | ......................... | 438/161 |
| 5,622,634 A * | 4/1997 | Noma et al. | ..................... | 216/40 |
| 5,869,922 A * | 2/1999 | Tolt | ................................ | 313/310 |
| 6,270,389 B1 * | 8/2001 | Kobayashi et al. | ............. | 445/24 |
| 6,781,166 B2 * | 8/2004 | Lieber et al. | ................... | 257/211 |
| 6,851,998 B2 * | 2/2005 | Aiba et al. | ........................ | 445/50 |
| 7,301,191 B1 * | 11/2007 | Tombler et al. | ............... | 257/296 |
| 7,301,199 B2 * | 11/2007 | Lieber et al. | ................... | 257/327 |
| 2004/0251813 A1 * | 12/2004 | Okai et al. | ..................... | 313/495 |
| 2005/0026531 A1 * | 2/2005 | Ohnuma | ........................ | 445/50 |
| 2006/0090996 A1 * | 5/2006 | Yaniv et al. | ............. | 204/157.15 |
| 2006/0175601 A1 * | 8/2006 | Lieber et al. | ..................... | 257/19 |
| 2008/0070162 A1 * | 3/2008 | Ufert | ............................. | 430/290 |
| 2008/0217732 A1 * | 9/2008 | Kreupl | .......................... | 257/528 |

FOREIGN PATENT DOCUMENTS

| | | |
|---|---|---|
| EP | 1096569 | 5/2001 |
| EP | 1892722 | 2/2008 |
| WO | 98/45847 | 10/1998 |

OTHER PUBLICATIONS

Araki, H. et al, Thin Solid films 1989, 187-194.*
Zhang, Y et al, Science 1998, 281, 973-975.*
Chen, J. et al, Science 1999, 286, 1550-1552.*
Shi, W.-S. et al, Advanced Materials 2000, 12, 1927-1930.*

(Continued)

*Primary Examiner* — Arlen Soderquist
(74) *Attorney, Agent, or Firm* — Winstead PC

(57) ABSTRACT

Electronic devices comprising a dielectric material, at least one carbon sheet, and two electrode terminals are described herein. The devices exhibit non-linear current-versus-voltage response over a voltage sweep range in various embodiments. Uses of the electronic devices as two-terminal memory devices, logic units, and sensors are disclosed. Processes for making the electronic devices are disclosed. Methods for using the electronic devices in analytical methods are disclosed.

58 Claims, 28 Drawing Sheets

OTHER PUBLICATIONS

Wu, K. et al, Journal of Applied Physics 2001, 90, 4810,-4814.*
Tour, J. M. et al, Journal of the American Chemical Society 2003, 125, 13279-13283.*
Wang, J. J. et al, Applied Physics Letters 2004, 85, 1265-1267.*
Fu, L. et al, Advances in Colloid and Interface Science 2004, 111, 133-157.*
Zhang, Y. et al, Applied Physics Letters 2005, 86, 073104-1-073104-3.*
French, B. L. et al, Jounal of Applied Physics 2005, 97, 114317-1-114317-8.*
Yuzvinsky, T. D. et al, Nano Letters 2006, 6, 2718-2722.*
Dragoman, M. et al, CAS 2007. International Semiconductor Conference, 2007, vol. 1, 53-56.*
Bhattacharyya, S. et al, Materials Science and Engineering C 2007, 27, 957-960.*
Kim, K. S. et al, IEEE Transactions on Plasma Science 2007, 35, 434-443.*
Ebbesen, T. W. et al, Nature 1996, 382, 54-56.*
Chico, L. et al, Physical Review B 1996, 54, 2600-2606.*
Fischer, J. E. et al, Physical Review B 1997, 55-58.*
Bockrath, M. et al, Science 1997, 275, 1922-1925.*
Ishibashi, K. et al, Physica E 2002, 13, 782-785.*
Husband, C. P. et al, IEEE Transactions on Electron Devices 2003, 50, 1865-1875.*
Feng, M. et al, Journal of the American Chemical Society 2005, 127, 15338-15339.*
Xiang, B. et al, Materials Letters 2006, 60, 754-756.*
Tran, E. et al, Advanced Materials 2006, 18, 1323-1328.*
Wen, Y. et al, Advanced Materials 2006, 18, 1983-1987.*
Scott, J. C. et al, et al, Advanced Materials 2007, 19, 1452-1463.*
Lemme, et al., "A graphene field-effect device", IEEE Electron Device Letters, 28:2007, pp. 282-284.
Morisaki, et al., "Memory-switching in amorphous carbon films", J. Non-Crys. Solids, 15:1974, pp. 531-534.
Han, et al., "Energy band-gap engineering of graphene nanoribbons", Phys. Rev. Lett. 98:2007, pp. 2068051-2068054.
Clough, et al., "Tetrahedrally bonded amorphous carbon (ta-C) thin film transistors", Electronics Lett., 32:1996, 498-499.
Echtermeyer, et al., "Nonvolatile switching in graphene field-effect devices", IEEE Electron Device Lett., 29:2008, pp. 952-954.
Standley, et al., "Graphene-based atomic-scale switches", Nano. Lett., 8:2008, pp. 3345-3349.
Johnson, et al., "512-Mb PROM with a three-dimensional array of diode/antifuse memory cells", IEEE J. Solid-State Circuits, 38:2003, pp. 1920-1928.
Li, et al., "Room-temperature negative differential conductance in carbon nanotubes", Carbon 43:2005, pp. 667-670.
Li, et al., "Negative differential resistance in tunneling transport through C60 encapsulated double-walled carbon nanotubes", Appl. Phys. Lett. 90:2007, pp. 0731061-0731063.
Larade, et al., "Conductance, I-V curves, and negative differential resistance of carbon atomic wires", Phys. Rev. B 64:2001, pp. 0754201-07542010.
Farajian, et al., "Nonlinear coherent transport through doped nanotube junctions", Phys. Rev. Lett. 82:1999, pp. 5084-5087.
Leonard, et al., "Negative differential resistance in nanotube devices", Phys. Rev. Lett. 85:2000, pp. 4767-4770.
Rueckes, et al., "Carbon nanotube-based nonvolatile random access memory for molecular computing", Science 289:2000, pp. 94-97.
Franklin, et al., "Integration of suspended carbon nanotube arrays into electronic devices and electromechanical systems", Appl. Phys. Lett. 81:2002, pp. 913-915.
Cha, et al., "Fabrication of a nanoelectromechanical switch using a suspended carbon nanotube", Appl. Phys. Lett. 86:2005, pp. 0831051-0831053.
Dujardin, et al., "Self-assembled switches based on electroactuated multiwalled nanotubes", Appl. Phys. Lett. 87:2005, pp. 1931071-1931073.
Deshpande, et al., "Carbon nanotube linear bearing nanoswitches", Nano Lett. 6:2006, pp. 1092-1095.
Jang, et al., "Nanoscale memory cell based on a nanoelectromechanical switched capacitor",. Nature Nanotech. 3:2008, pp. 26-30.
Wang, et al., "Room-temperature all-semiconducting sub-10-nm graphene nanoribbon field-effect transistors", Phys. Rev. Lett. 100:2008, pp. 2068031-20680314.
Collins, et al., "Current saturation and electrical breakdown in multiwalled carbon nanotubes", Phys. Rev. Lett. 86:2001, pp. 3128-3131.
Li, et al., "SiC-SiO2-C coaxial nanocables and chains of carbon nanotube-SiC heterojunctions", Adv. Mater. 16:2004, pp. 93-96.

* cited by examiner

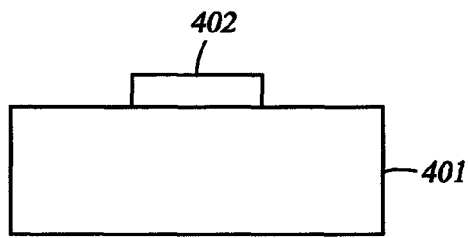
Fig. 4A         Fig. 4B
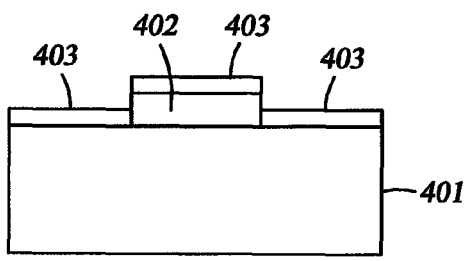
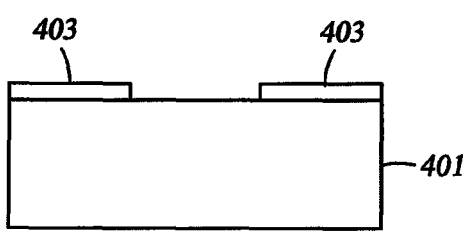
Fig. 4C         Fig. 4D
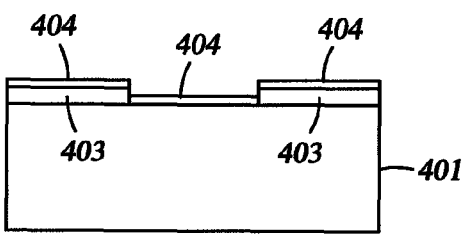
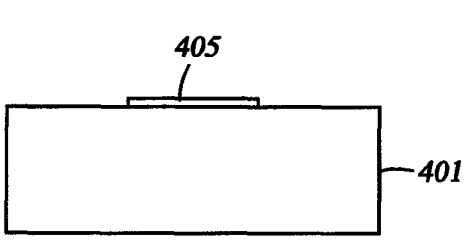
Fig. 4E         Fig. 4F
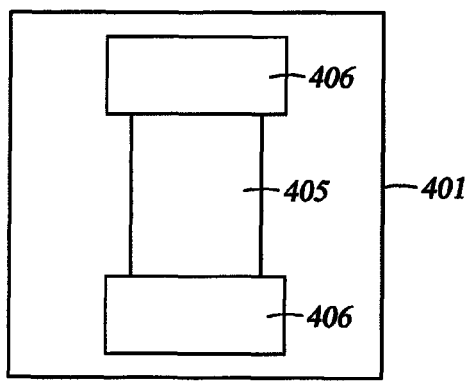
Fig. 4G

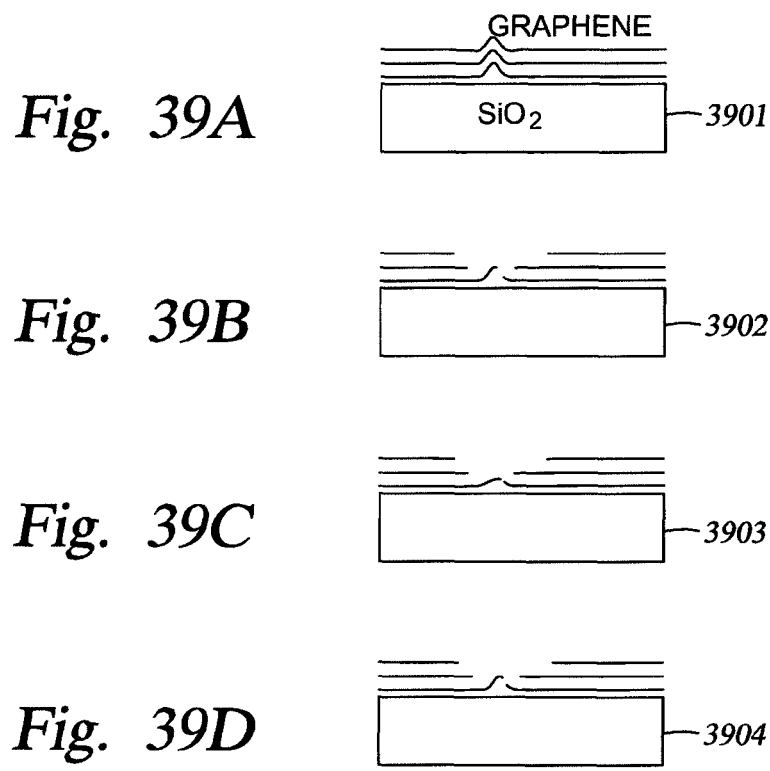
Fig. 39A
Fig. 39B
Fig. 39C
Fig. 39D
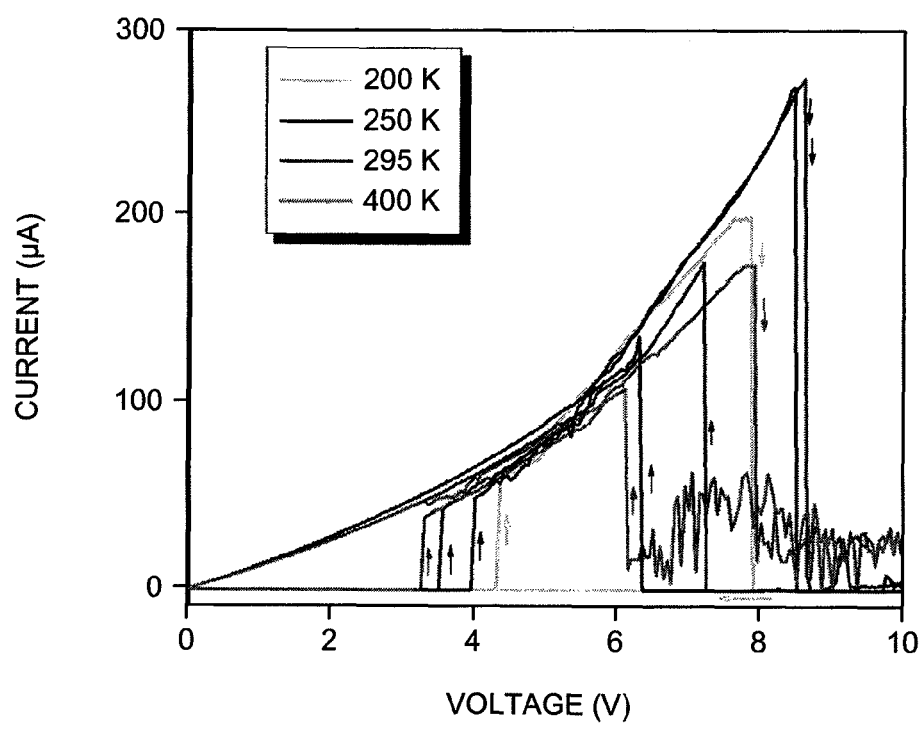
Fig. 40

TABLE 1: DEPENDENCE OF Vth AND PVR ON C-SiO-SiC NANOCABLE CHANNEL LENGTH

| NANOCABLE CHANNEL LENGTH (μm) | NEGATIVE BIAS $V_{th}$ (V) | POSITIVE BIAS $V_{th}$ (V) | NEGATIVE BIAS PVR | POSITIVE BIAS PVR |
|---|---|---|---|---|
| 3.5 | -9.6 | +10.4 | 6000 | $1.7 \times 10^6$ |
| 2.7 | -9.0 | +9.0 | N/D | $1.3 \times 10^4$ |
| 2.8 | -8.0 | +7.2 | 6700 | 6700 |
| 4.5 | -6.6 | +8.4 | 2800 | $4.7 \times 10^5$ |
| 0.70 | -4.8 | +5.2 | 2400 | 6500 |
| 0.43 | -4.0 | +4.2 | 86000 | 7100 |
| 0.28 | -4.0 | +3.9 | 1300 | 3000 |

Fig. 44

ELECTRONIC SWITCHING, MEMORY, AND SENSOR DEVICES FROM A DISCONTINUOUS GRAPHENE AND/OR GRAPHITE CARBON LAYER ON DIELECTRIC MATERIALS

CROSS-REFERENCE TO RELATED APPLICATIONS

This application claims priority to U.S. provisional patent applications 60/976,143 filed Sep. 28, 2007 and 60/982,329 filed Oct. 24, 2007 which are incorporated by reference as if written herein in their entirety.

STATEMENT REGARDING FEDERALLY SPONSORED RESEARCH

This invention was made with government support under Grant No. NCC-001-0203, awarded by the National Aeronautics and Space Administration; and Grant No. W911NF-08-C-0019, awarded by the U.S. Department of Defense. The government has certain rights in the invention.

BACKGROUND

Transistors are a bulwark of electronic switching and memory applications due to their extreme reliability and high ON/OFF ratios of $10^4$-$10^5$. Transistors are three-terminal devices that include source, drain, and gate electrode terminals. Corresponding two-terminal electronic devices, having a source and a drain, typically have ON/OFF ratios that are orders of magnitude smaller than transistors. Two-terminal electronic devices can be operable in switching and memory applications, provided the devices display a non-linear current-versus-voltage response and have a great enough and reliable ON/OFF ratio.

Molecular-based devices and one-dimensional carbon nanostructures having non-linear current-versus-voltage response and current peak-to-valley ratios (PVRs) generally on the order of 2 to 100 have been reported. Likewise, two-terminal memory devices have been described that are based upon metal filamentary mechanisms. These include molecular-spaced devices, nanowire crossbar memories, and resistive random access memories using transition metal oxides. Coaxial multi-layer nanocables, which may include various materials, including carbon nanotubes, are of potential interest in molecular-based devices, since nanocables retain the one-dimensional features of both nanowires and nanotubes in the axial direction and form a heterojunction in the radial direction.

In view of the foregoing, development of electronic devices exhibiting nonlinear current-versus-voltage response, further characterized by a negative differential resistance region, and having high and reliable ON/OFF ratios characterized by large current PVRs would be of substantial benefit. Such devices may have applications in electronic switching, memory, and sensor applications. In memory applications, devices having stable, re-writable, non-volatile, and non-destructive read memories with fast switching times would be of substantial benefit in countless electronics applications where computer memory is used.

SUMMARY

In various embodiments, electronic devices are disclosed. The electronic devices include a dielectric material, at least one carbon sheet, and two electrode terminals. The at least one carbon sheet is deposited on the dielectric material. A first of the two electrode terminals forms a source and a second of the two electrode terminals forms a drain. The electronic devices exhibit nonlinear current-versus-voltage response when operated over a voltage sweep range. In some embodiments, the electronic devices may, for example, be used as two-terminal memory devices, logic switches, and sensors.

In other various embodiments, electronic devices are prepared by a process including: 1) providing a dielectric material; 2) depositing at least one carbon sheet on the dielectric material; and 3) positioning two electrode terminals on the dielectric material. In various embodiments, the at least one carbon sheet lies between the two electrode terminals. A first of the two electrode terminals forms a source and a second of the two electrode terminals forms a drain. In some embodiments, the electronic device prepared by the process further includes applying a voltage sweep between the two electrode terminals, such that the voltage sweep produces a nonlinear current-versus-voltage response.

In other various embodiments, analytical methods are disclosed. The methods comprise: 1) providing an electronic device; 2) operating the electronic device over a voltage sweep range; and 3) observing current-versus-voltage performance of the electronic device. The operating and observing steps occur in the presence of at least one analyte.

The foregoing has outlined rather broadly various features of the present disclosure in order that the detailed description that follows may be better understood. Additional features and advantages of the disclosure will be described hereinafter, which form the subject of the claims.

BRIEF DESCRIPTION OF THE DRAWINGS

For a more complete understanding of the present disclosure, and the advantages thereof, reference is now made to the following descriptions to be taken in conjunction with the accompanying drawings describing a specific embodiment of the disclosure, wherein:

FIG. 4 shows an embodiment of a two-terminal electronic device and exemplary process steps for preparing the device.

FIG. 39 shows an embodiment of a proposed NEM switching mechanism responsible for BIV behavior in graphenic or graphitic nanocable electronic devices.

FIG. 40 shows embodiments of BIV behavior for a C—SiO$_2$ nanocable electronic device over a temperature range between 200 K and 400 K.

FIG. 44 shows a summary of embodiments of the dependence of $V_{th}$ and PVR on C—SiO$_2$—SiC nanocable channel length.

DETAILED DESCRIPTION

Figure 1A:
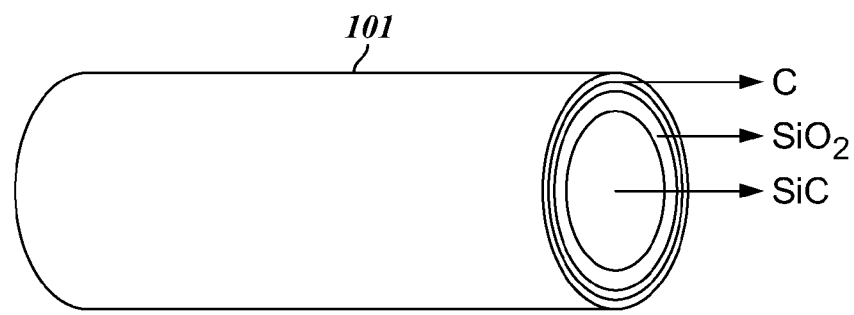
FIG. 1 shows an embodiment of C—$SiO_2$—SiC, C—$SiO_2$—Si, and C—$SiO_2$ nanocables.

In the following description, certain details are set forth such as specific quantities, sizes, etc. so as to provide a thorough understanding of the various embodiments disclosed herein. However, it will be obvious to those skilled in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

Referring to the drawings in general, it will be understood that the illustrations are for the purpose of describing a particular embodiment of the disclosure and are not intended to be limiting thereto. Drawings are not necessarily to scale.

While most of the terms used herein will be recognizable to those of skill in the art, the following definitions are nevertheless put forth to aid in the understanding of the present disclosure. It should be understood, however, that when not explicitly defined, terms should be interpreted as adopting a meaning presently accepted by those of skill in the art.

"Bias," as defined herein, is a predetermined voltage applied to an electronic device that causes the device to operate in a certain desired fashion or to set a certain operating point. In the various embodiments presented herein, a voltage bias may be established at the source electrode terminal or through a third electrode not comprising the source or drain electrode terminals.

"Channel length," as defined herein, refers to the length of at least one carbon sheet bridging between source and drain electrodes of the electronic devices described herein. In other words, channel length is the inter-electrode separation distance.

"Discontinuous carbon layer," as defined herein, refers to a discontinuous graphene layer or discontinuous graphite layer between source and drain electrodes, where at least two independent sheets of graphene or graphite span the distance between the source and drain electrodes, because no one sheet of graphene or graphite is long enough to completely span the distance between the source and drain electrodes. In forming the discontinuous graphene layer or discontinuous graphite layer, the at least two independent sheets of graphene or graphite have at least one overlapping region between the sheets.

"Negative differential resistance (NDR)," as defined herein, is a current decrease in response to an increase in the bias voltage applied across a two-terminal device. A mechanistic origin of the effect is sometimes implied in certain descriptions of materials having NDRs. As used herein, the term "bistable current-voltage (BIV) behavior," is used to describe an NDR-like effect, where no mechanistic implications are made.

"Peak-to-valley ratio (PVR)," as defined herein, is the ratio of maximum current response obtained within a given voltage sweep to minimum current response obtained within the sweep.

"Threshold voltage ($V_{th}$)," as defined herein, is the voltage at which a maximum or minimum current peak occurs in a device exhibiting BIV behavior.

Figure 1B:
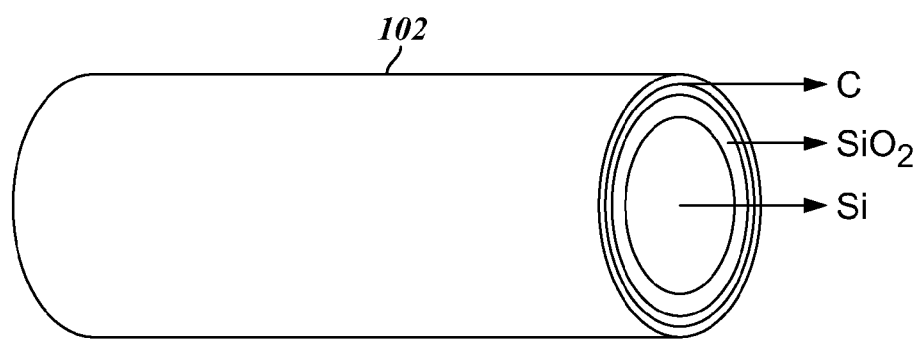
Figure 1C:
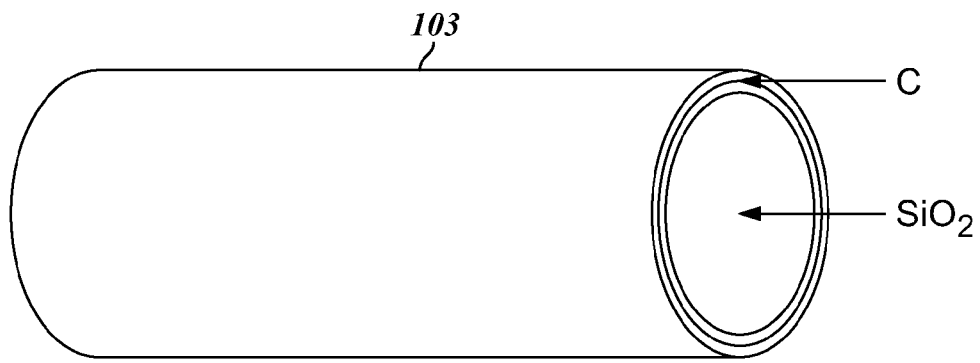
Figure 2:
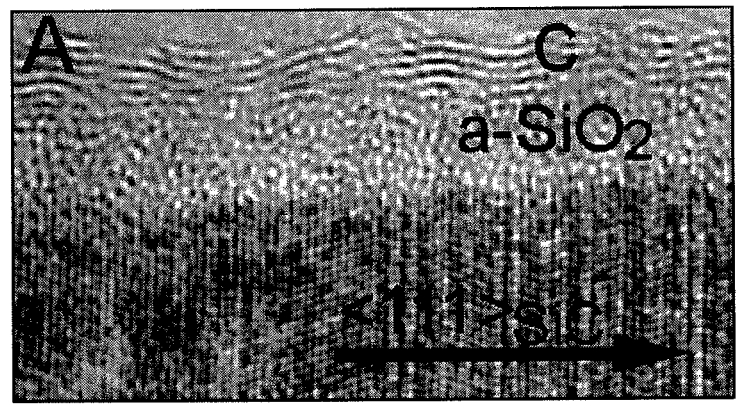
FIG. 2 shows a high-resolution TEM image of a C—$SiO_2$—SiC nanocable embodiment.
Figure 3:
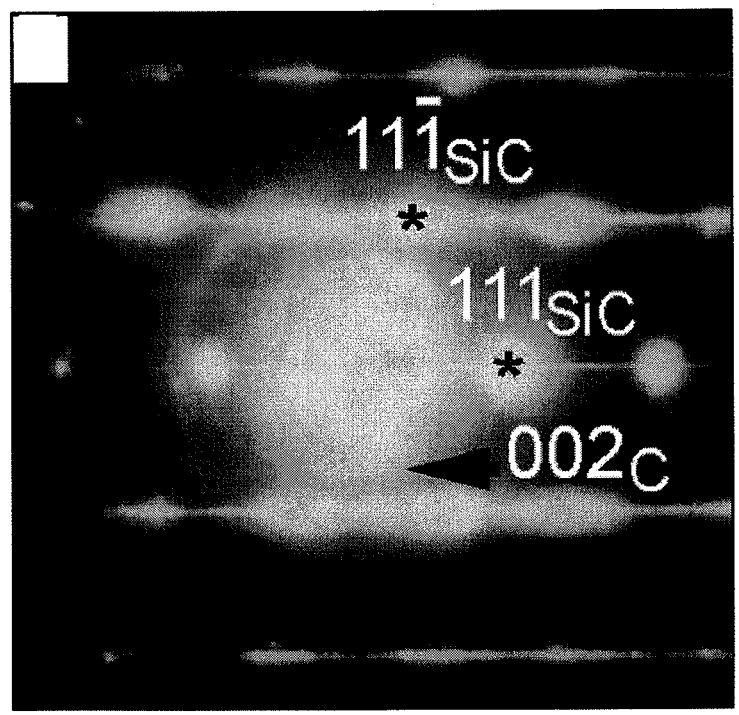
FIG. 3 shows a selected-area electron diffraction pattern of a C—$SiO_2$—SiC nanocable embodiment.

In some of the embodiments of electronic devices disclosed herein, the electronic devices include at least one nanocable. Nanocables may be formed from coaxial sheets of carbon and a dielectric material in an embodiment. In another embodiment, a nanowire core optionally further comprises the nanocables. Exemplary but non-limiting nanocables utilized in the various embodiments presented herein include C—SiO$_2$—SiC, C—SiO$_2$—Si, and C—SiO$_2$ nanocables. The nanocables may be represented in a generic form X—Y—Z. In this generic representation, a layer of dielectric material Y is covered by at least one carbon sheet of layer X. Z is an optional nanowire core component of the nanocable housed within dielectric material Y. For example, nanocable C—SiO$_2$—SiC includes a SiC nanowire core, covered by a SiO$_2$ dielectric coating, which is in turn covered by at least one carbon sheet. In various embodiments described herein, C may, for example, refer to graphite, graphene, or graphene sheets. FIG. 1 shows pictorial representations of the three types of nanocables. In FIG. 1, 101 is a C—SiO$_2$—SiC nanocable, 102 is a C—SiO$_2$—Si nanocable, and 103 is a C—SiO$_2$ nanocable. Embodiments of a C—SiO$_2$—SiC nanocable high-resolution TEM image and corresponding selected-area electron diffraction pattern are respectively presented in FIGS. 2 and 3. Further description of the nanocable devices used within the present disclosure are provided as experimental examples hereinbelow.

In some embodiments herein, an electronic device is disclosed. The electronic device includes a dielectric material, at least one carbon sheet, and two electrode terminals. In an embodiment, the at least one carbon sheet is deposited on the dielectric material. In an embodiment, a first of the two electrode terminals forms a source and a second of the electrode terminals forms a drain. In various embodiments, the electronic device exhibits nonlinear current-versus-voltage response when operated over a voltage sweep range between the source and drain electrodes. In various embodiments, the at least one carbon sheet comprising the electronic device forms a discontinuous carbon layer. The discontinuous carbon layer may be comprised by graphene sheets or graphite sheets in an embodiment. The discontinuous carbon layer is advantageous for fabricating certain embodiments of the electronic device, since the discontinuous carbon layer may be formed by, for example, chemical vapor deposition.

The at least one carbon sheet comprising the electronic device may be in a form that includes, but is not limited to, graphite, graphene, and graphene sheets. In some embodiments of the electronic device, the at least one carbon sheet is selected from a group consisting of graphene, graphite, and combinations thereof. The dielectric material forming the electronic device may include, but is not limited to, silicon dioxide, silicon nitride, ceramics, glass, and plastic. In some embodiments of the electronic device, the dielectric material is selected from a group consisting of silicon dioxide, silicon nitride, glass, and plastic.

In certain embodiments of the electronic device, the device further includes a semiconductor. In some embodiments, the dielectric material maintains continuous contact with the semiconductor. In some embodiments disclosed herein, the semiconductor comprises a stacked silicon-on-insulator structure. Such arrangements are well known to those of skill in the relevant art. Semiconductors may be elemental semiconductors, binary semiconductors, ternary semiconductors, ternary semiconductor alloys, quaternary semiconductor alloys, quinary semiconductor alloys, and organic semiconductors.

Exemplary but non-limiting semiconductor materials may include, but are not limited to, diamond, silicon, germanium, silicon carbide, silicon germanide, aluminium antimonide, aluminium arsenide, aluminium nitride, aluminium phosphide, boron nitride, boron phosphide, boron arsenide, gallium antimonide, gallium arsenide, gallium nitride, gallium phosphide, indium antimonide, indium arsenide, indium nitride, indium phosphide, cadmium selenide, cadmium sulfide, cadmium telluride, zinc oxide, zinc selenide, zinc sulfide, zinc telluride, lead selenide, lead sulfide, lead telluride, tin sulfide, tin telluride, bismuth telluride, cadmium phosphide, cadmium arsenide, cadmium antimonide, zinc phosphide, zinc arsenide, zinc antimonide, lead(II) iodide, molybdenum disulfide, gallium selenide, tin sulfide, bismuth sulfide, copper indium gallium selenide, platinum silicide, bismuth(III) iodide, mercury(II) iodide, thallium(I) bromide, aluminium gallium arsenide, indium gallium arsenide, indium gallium phosphide, aluminium indium arsenide, aluminium indium antimonide, gallium arsenide nitride, gallium arsenide phosphide, aluminium gallium nitride, aluminium gallium phosphide, indium gallium nitride, indium arsenide antimonide, indium gallium antimonide, aluminium gallium indium phosphide, aluminium gallium arsenide phosphide, indium gallium arsenide phosphide, aluminium indium arsenide phosphide, aluminium gallium arsenide nitride, indium gallium arsenide nitride, indium aluminium arsenide nitride, gallium arsenide antimonide nitride, gallium indium nitride arsenide antimonide, gallium indium arsenide antimonide phosphide, cadmium zinc telluride, mercury cadmium telluride, mercury zinc telluride, mercury zinc selenide, lead tin telluride, thallium tin telluride, and thallium germanium telluride. Organic semiconductors suitable for practicing the disclosure may include single molecules, oligomers, and semiconducting polymers. Exemplary but non-limiting organic semiconductors that may be used in practice of the embodiments disclosed herein may include pentacene, anthracene, rubrene, poly(thiophene)s, poly(aniline)s, poly(pyrrole)s, poly(p-phenylene vinylene), poly(acetylene), and derivatives and combinations thereof. In certain embodiments of the electronic device, the semiconductor is selected from a group consisting of silicon, silicon carbide, gallium arsenide, and germanium.

In certain embodiments of the electronic device, a gate electrode further comprises the electronic device. In various embodiments, a gate electrode distinct from the source and the drain electrode terminals further comprises the electronic device. In these various embodiments, the gate electrode influences performance of the semiconductor. In an embodiment, the gate electrode may be constructed on a material such as, but not limited to, silicon-on-insulator (SOI). Gated operation of the electronic device may beneficially alter the performance of the device in an embodiment.

A number of different methods may be used to deposit the at least one carbon sheet on the electronic device. The suitability of a particular technique will be dependent on the nature of the at least one carbon sheet being deposited and will be evident to one skilled in the art. In certain embodiments, the at least one carbon sheet is deposited from a gas comprising at least one carbon-containing compound. In further embodiments, the gas comprises hydrogen. The at least one carbon-containing compound may be selected from a group consisting of acetylene, ethylene, methane, ethane, carbon monoxide, and combinations thereof in various embodiments. In certain embodiments, the at least one carbon sheet is deposited at a temperature between about 400° C. and about 900° C. In other embodiments, the at least one carbon sheet is deposited at a temperature between about 800° C. and about 900° C. In some embodiments, the at least one carbon sheet is deposited by a process selected from a group consisting of ink-jet printing and solution-spin coating. Material deposited by the ink-jet printing and solution-spin coating techniques may be selected from a group consisting of exfoliated graphene, graphite, or combinations thereof in an embodiment.

The source and drain electrode terminals may be formed from various conductor or semiconductor materials in constructing the electronic devices. Exemplary, but non-limiting, materials that may be used to form the source and drain may be selected from a group consisting of platinum, palladium, gold, silver, silicon, gallium arsenide, titanium, tin, copper, and combinations thereof in an embodiment. Selection of the materials for constructing the source and drain electrodes is conducted independently. One skilled in the art will recognize that the properties of the various electrode materials may confer advantageous properties to certain embodiments of the electronic device, and all such combinations of materials are fully within the spirit and scope of the present disclosure.

Certain electrical properties of the electronic devices disclosed herein give the devices advantageous benefits, particularly as two-terminal devices for switching and memory applications. The devices disclosed herein exhibit BIV behavior and high PVRs in their current-versus-voltage response. Further, the transition from a low conduction state to a high conduction state is characterized by a sharp threshold voltage ($V_{th}$) occurring over a very narrow voltage transition. Although the switching and memory performance of the devices is somewhat variable from device to device based on variations in construction parameters, the electronic devices provide considerably advanced properties over existing two-terminal devices. All such operational variation lies within the spirit and scope of the disclosure. Parameters which may affect the switching and memory performance of the electronic devices may include, but are not limited to, separation between the electrode terminals (channel length), dielectric material thickness, and thickness of the at least one carbon layer. Threshold voltages are typically in the range of 6-12 V for devices with a channel length of 2-5 μm and below 5 V for devices with a channel length of <1 μm. ON/OFF switching ratios of $10^4$ to $10^6$ are typically observed. The operational parameters presented hereinabove are merely exemplary and should not be considered limiting.

In certain embodiments of the electronic device, the nonlinear current-versus-voltage response includes at least about a 10-fold change in current over a voltage sweep range of about 0.5 V. In other embodiments of the electronic device, the nonlinear current-versus-voltage response includes a change in current between about 10-fold and $10^9$-fold over a voltage sweep range of about 0.5 V. In still other embodiments of the electronic device, the nonlinear current-versus-voltage response includes a change in current between about $10^5$-fold and $10^9$-fold over a voltage sweep range of about 0.5 V. These operational characteristics beneficially provide high PVRs and ON/OFF ratios in operation of the devices.

In some embodiments, the electronic device is operated over a voltage sweep range of less than about 15 V. In other embodiments, the electronic device is operated over a voltage sweep range of less than about 5 V. In still other embodiments, the electronic device is operated over a voltage sweep range of less than about 1 V.

In certain embodiments, the electronic device comprises a two-terminal memory device having an ON/OFF memory state. In some embodiments, the electronic device has an ON/OFF ratio of at least about 100:1 for measuring recorded currents in the ON and OFF states. High ON/OFF ratios are characteristic of the electronic devices as a result of their beneficial electronic properties noted hereinabove. The ON/OFF ratios characteristic of the electronic devices make the devices well suited in applications in which two-terminal memory may be used.

Additional components may characterize the electronic device disclosed herein. In certain embodiments, the electronic device is constructed on a planar silicon wafer. In certain other embodiments, a gate electrode further comprises the electronic device. In some embodiments, the gate electrode is above the at least one carbon layer. In other embodiments, the gate electrode is below the at least one carbon layer. In the various embodiments, the gate electrode may modify current flow through the carbon sheet. The electronic device may also include at least one nanowire in an embodiment. In various embodiments, the at least one nanowire lies between the source and the drain electrode terminals. Nanowires may be formed from several different types of nanomaterials and may be metallic, semiconducting, or insulating. Nanowires may be formed from either organic or inorganic materials, the choice of which and methods for formation thereof are well known to those versed in the relevant art.

In some embodiments, the electronic device comprises at least one nanocable. In some embodiments, the at least one nanocable lies between the source and the drain electrode terminals. In some embodiments, the at least one nanocable comprises at least two layers. In an embodiment, the at least one nanocable comprises two layers. In another embodiment, the at least one nanocable comprises three layers. An exemplary but non-limiting two-layer nanocable presented herein is a C—$SiO_2$ nanocable, which is defined and described hereinabove. Exemplary three-layer nanocables include, but are not limited to, C—$SiO_2$—SiC and C—$SiO_2$—Si nanocables. Applicability of a particular nanocable for a given embodiment of the electronic device will be evident to one skilled in the art in view of the experimental examples presented hereinbelow.

In some embodiments, the electronic device comprises a sensor. Operating the electronic device as a sensor may allow the electronic device to detect a wide range of molecules based on alteration of the observed electrical properties or BIV behavior of the device. As a non-limiting example, a molecule may become adsorbed to the at least one carbon sheet of the device and alter its electrical properties or BIV behavior. Such adsorption comprises an embodiment of non-covalent bonding. Alternatively, a molecule may become covalently bound to the at least one carbon sheet of the device and alter its electrical properties or BIV behavior. One skilled in the art will recognize that a wide range of molecules may be detected when the electronic device is operated as a sensor. Further, one skilled in the art will recognize that the at least one carbon sheet may be modified to alter its affinity for a given molecule, either in its low-conductance state, high-conductance state, or both low and high-conductance states. Methods for modifying carbon sheets, such as graphene and graphite, are well known in the art, and any of these modification methods may be combined to provide affinity of the at least one carbon layer toward a given molecule.

Exemplary but non-limiting chemistries for modifying the carbon sheets may include the Billups reaction or Tour diazonium-based functionalization. The Billups reaction includes reaction of the carbon sheet with an alkali metal, such as Li or Na, in liquid ammonia, followed by reaction with an electrophile, such as an alkyl halide, aryl halide, or carbonyl. The Tour diazonium-based functionalization includes a radical-based introduction of aryl groups to the graphene or graphite sheet. Related chemistries for covalently introducing functional groups to carbon nanotubes may be envisioned for functionalizing carbon sheets by those skilled in the art In certain embodiments of the electronic devices and sensors derived therefrom, the at least one carbon sheet is chemically functionalized with covalent bonds. As described hereinabove, methods for functionalizing carbon sheets are well known to those of skill in the relevant art. The covalent bonds may attach to a component selected from a group including, but not limited to, alkyl groups, aryl groups (arenes), halides, carboxylic acids, amines, substituted amines, amides, carboxylic esters, sulfonic acids, sulfonamides, alkoxy groups, and aryloxy groups. The at least one carbon sheet may be bonded to a group capable of coordinating a metal ion, such as but not limited to a chelating group. When a chelating group is bound to the at least one carbon sheet, the electronic devices or sensors derived therefrom may be particularly beneficial in applications for sensing metal ions. Functionalized graphene or graphite sheets may be covalently attached to biomolecules including, but not limited to, nucleic acids, DNA, RNA, oligonucleotides, polynucleotides, nucleosides, nucleotides, amino acids, peptides, oligopeptides, polypeptides, proteins, glycoproteins, enzymes, lipids, phospholipids, glycolipids, hormones, peptide hormones, neurotransmitters, carbohydrates, sugars, monosaccharides, disaccharides, trisaccharides, oligosaccharides, polysaccharides, antibodies, antibody fragments, and synthetic derivatives and analogs thereof. The non-limiting functionalizations presented hereinabove may be used to alter the affinity of the at least one carbon sheet toward binding of a given molecule, biomolecule, or analyte. The functionalizations may themselves alter the electrical properties of the at least one carbon sheet or provide greater affinity toward binding of a particular molecule, biomolecule, or analyte. In various embodiments of the electronic devices or sensors derived therefrom, covalent bonds connect the at least one carbon sheet to at least one moiety chosen from a group consisting of alkyls, arenes, saccharides, peptides, nucleotides, halides, and combinations thereof.

In certain embodiments, operation of the electronic devices or sensors derived therefrom within the voltage sweep range promotes chemical functionalization of the at least one carbon sheet with covalent bonds. In some embodiments, chemical functionalization with covalent bonds may comprise functionalization of the at least one carbon sheet of the electronic devices or sensors derived therefrom, where the at least one carbon sheet is not previously functionalized with covalent bonds. In other embodiments, chemical functionalization with covalent bonds may comprise functionalization of the at least one carbon sheet of the electronic device or sensors derived therefrom, where the at least one carbon sheet previously comprised covalent bonds and is further modified. In certain embodiments, operation of the electronic devices or sensors derived therefrom within the voltage sweep range promotes further modification through non-covalent bonding.

In certain embodiments, the carbon sheets coating the electronic device or sensors derived therefrom may adsorb molecules. In other words, the carbon sheets are modified through non-covalent bonding. The adsorbed molecules may change the electronic properties of the electronic devices or sensors derived therefrom. Adsorbed molecules may comprise alkyl groups, aryl groups (arenes), halides, carboxylic acids, amines, substituted amines, amides, carboxylic esters, sulfonic acids, sulfonamides, alkoxy groups, aryloxy groups, and styrenes. As such, in an embodiment, the electronic devices or sensors derived therefrom may be used for detecting a range of analytes based on changes in the observed BIV characteristics upon adsorption or desorption of molecules. Likewise, the carbon sheets may adsorb any of the biomolecules listed hereinabove to improve sensor sensitivity. In an embodiment of the electronic device or sensors derived therefrom, the at least one carbon sheet is modified through non-covalent bonding. In various embodiments, non-covalent bonding comprises adsorption of at least one moiety to the at least one carbon sheet. In various embodiments of the electronic devices or sensors derived therefrom, the at least one moiety is chosen from a group consisting of alkyls, arenes, saccharides, peptides, nucleotides, halides, styrenes, and combinations thereof.

In certain embodiments, operation of the electronic devices or sensors derived therefrom within the voltage sweep range promotes chemical functionalization of the at least one carbon sheet with non-covalent bonds. Non-covalent bonds may comprise adsorption of at least one molecule in an embodiment. In various embodiments, chemical functionalization with non-covalent bonds may comprise functionalization of the at least one carbon sheet of the electronic devices or sensors derived therefrom, where the at least one carbon sheet is not previously functionalized with non-covalent bonds. In other embodiments, chemical functionalization with non-covalent bonds may comprise functionalization of the at least one carbon sheet of the electronic devices or sensors derived therefrom, where the at least one carbon sheet previously comprised non-covalent bonds and is further modified. In certain embodiments, operation of the electronic devices or sensors derived therefrom within the voltage sweep range promotes further modification through non-covalent bonding.

In various embodiments of the electronic devices or sensors derived therefrom, operation of the electronic device within the voltage sweep range promotes displacement of at least one molecule from the at least one carbon sheet comprising the electronic devices or sensors derived therefrom. In some embodiments, the at least one molecule displaced is covalently bound to the at least one carbon sheet. In other embodiments, the at least one molecule displaced is non-covalently bound to the at least one carbon sheet. In some embodiments, the at least one molecule displaced is adsorbed to the at least one carbon sheet. In certain embodiments, the at least one molecule displaced comprises at least one analyte.

In certain embodiments of the electronic device, the electronic device comprises a logic switch. In some embodiments, the electronic device comprises a logic switch, where the electronic device further comprises a gate electrode above the at least one carbon sheet of the device. In some other embodiments, the electronic device comprises a logic switch, where the electronic device further comprises a gate electrode below the at least one carbon sheet of the device. In any of the various embodiments comprising a gate electrode, the gate electrode modifies current flow through the at least one carbon sheet of the electronic device comprising the logic switch.

In certain embodiments herein, analytical methods are presented. The analytical methods comprise: 1) providing the electronic device described hereinabove; 2) operating the electronic device over a voltage sweep range, where the operating step occurs in the presence of at least one analyte; and 3) observing current-versus-voltage performance of the electronic device in the presence of the at least one analyte. In various embodiments, the at least one analyte becomes bound to the at least one carbon sheet of the electronic device. In some embodiments, the methods further comprise removing the at least one analyte from the as least one carbon sheet after the operating step. In still other embodiments, the methods comprise comparing the current-versus-voltage performance of the electronic device in the absence of the at least one analyte to the current-versus-voltage performance of the electronic device in the presence of the at least one analyte as described hereinabove. Such operation of the electronic device in the absence of an analyte permits the background performance of the electronic device to be obtained. When the electronic device is responsive to the presence of the at least one analyte, the magnitude of response of the electronic device may be proportional to the quantity of at least one analyte present. Operation of the device in the presence of known quantities of the at least one analyte may allow the electronic device to quantitate an unknown amount of the at least one analyte present. Non-limiting techniques whereby such quantitation may be performed include calibration curve techniques and standard additions techniques. Analytical methods utilizing these techniques are within the capabilities of those having skill in the art. Use of the electronic devices described hereinabove in analytical methods using these techniques are within the capabilities of the ordinarily skilled artisan.

In other various embodiments, an electronic devices are prepared by a process comprising: 1) providing a dielectric material; 2) depositing at least one carbon sheet on the dielectric material; and 3) positioning two electrode terminals on the dielectric material, where the at least one carbon sheet lies between the two electrode terminals. In various embodiments, the electronic devices are prepared by a process that further comprises: applying a voltage sweep between the two electrode terminals, wherein the voltage sweep produces a nonlinear current-versus-voltage response. In the various embodiments of the electronic devices prepared by the process presented hereinabove, a first of the two electrode terminals comprises a source and a second of the two electrode terminals comprises a drain. In various embodiments of the electronic devices prepared by the process presented hereinabove, the at least one carbon sheet forms a discontinuous carbon layer.

In some embodiments of the electronic devices prepared by the process disclosed hereinabove, the at least one carbon sheet may be in a form that includes, but is not limited to graphite, graphene sheets, and graphene. In certain embodiments of the electronic devices prepared by the process disclosed hereinabove, the at least one carbon sheet is selected from a group consisting of graphene and graphite.

In some embodiments of the electronic devices prepared by the process disclosed hereinabove, the dielectric material may include, but is not limited to, silicon dioxide, silicon nitride, ceramics, glass, and plastic. In certain embodiments of the electronic devices prepared by the process disclosed hereinabove, the dielectric material is selected from a group consisting of silicon oxide, silicon nitride, glass, and plastic. In certain embodiments of the electronic devices prepared by the process disclosed hereinabove, the dielectric material maintains continuous contact with a semiconductor. Semiconductors suitable for use in the process of preparing the product include, but are not limited to, any of the semiconductors previously listed hereinabove. In certain embodiments of the electronic devices by the process disclosed hereinabove, the semiconductor is selected from a group consisting of silicon, silicon carbide, gallium arsenide, and germanium. In some embodiments of the electronic devices prepared by the process disclosed hereinabove, the process further comprises attaching a gate electrode to the electronic device. In various embodiments of the electronic devices prepared by the process disclosed hereinabove, the performance of the semiconductor is influenced by a gate electrode. In any of the embodiments of the electronic device prepared by the process disclosed hereinabove, the gate electrode is distinct from the source and drain electrode terminals.

The electronic devices prepared by the process disclosed herein may utilize several different methods to deposit the at least one carbon sheet on the electronic device. In some embodiments of the electronic devices, the process for forming the at least one carbon sheet of the devices comprises a depositing step performed with a gas comprising at least one carbon-containing compound. Suitable carbon-containing compounds may include, but are not limited to, acetylene, ethylene, methane, ethane, carbon monoxide, and combinations thereof. Deposition of the at least one carbon sheet may occur at a temperature between about 400° C. and about 900° C. in various embodiments. In other embodiments, deposition of the at least one carbon sheet may occur at a temperature between about 800° C. and about 900° C. In some embodiments of the electronic devices, the process for forming the at least one carbon sheet of the device comprises a depositing step performed by ink-jet printing. In other embodiments of the electronic devices, the process for forming the at least one carbon sheet of the device comprises a depositing step performed by solution-spin coating. In embodiments of the electronic devices prepared by a process comprising ink-jet printing or solution-spin coating techniques, the at least one carbon sheet deposited by the technique may comprise graphene, graphite, or combinations thereof. The graphite or graphene may be previously exfoliated.

The electronic devices prepared by the process disclosed herein may utilize several different materials in constructing the two electrode terminals comprising the electronic device. In some embodiments of the electronic devices prepared by the process disclosed herein, positioning the two electrodes comprises constructing the two electrodes from at least one material selected from a group consisting of platinum, palladium, gold, silver, silicon, gallium arsenide, titanium, tin, copper, and combinations thereof. In the process of constructing the source and drain electrode terminals comprising the electronic devices, the selections of the at least one material for the source and for the drain are conducted independently of one another.

In embodiments of the electronic devices prepared by the process disclosed hereinabove, the process comprises applying a voltage sweep between the two electrode terminals comprising the device. In embodiments of a working device, the voltage sweep produces a nonlinear current-versus-voltage response. Application of a voltage sweep in preparing the electronic device may comprise a means whereby quality of the device fabrication is monitored. For example, in representative examples of the electronic devices not displaying BIV behavior, subsequent analyses of the electronic devices have revealed a simple open or closed circuit. Application of a voltage sweep during electronic device fabrication may also comprise setting the electronic device into an initial conduction state for further processing. In a further example, applying a voltage sweep in preparing the electronic device may comprise a means of functionalizing the at least one carbon sheet with at least one molecule. Functionalizing the at least one carbon sheet may comprise a covalent modification of the at least one carbon sheet during the step of applying a voltage sweep. Functionalizing the at least one carbon sheet may also comprise a non-covalent modification of the at least one carbon sheet. An exemplary state of non-covalent modification may include, but is not limited to, adsorption of at least one molecule to the carbon sheet.

In certain embodiments of the electronic devices prepared by the process disclosed hereinabove, a nonlinear current-versus-voltage response comprises at least about a 10-fold change in current over a voltage sweep range of about 0.5 V. In other embodiments of the electronic devices prepared by the process disclosed hereinabove, a nonlinear current-versus-voltage response comprises a change in current between about 10-fold and $10^9$-fold over a voltage sweep range of about 0.5 V. In still other embodiments of the electronic devices prepared by the process disclosed hereinabove, a nonlinear current-versus-voltage response comprises a change in current between about $10^5$-fold and $10^9$-fold over a voltage sweep range of about 0.5 V.

In certain embodiments of the electronic devices prepared by the process disclosed hereinabove, the process further comprises placing a gate electrode above the at least one carbon sheet. In certain other embodiments of the electronic devices prepared by the process disclosed hereinabove, the process further comprises placing a gate electrode below the at least one carbon sheet. In various embodiments, the gate electrode modifies current flow through the at least one carbon sheet.

In certain embodiments, the electronic devices prepared by the process disclosed hereinabove further comprise chemically functionalizing the at least one carbon sheet with covalent bonds. Such functionalization with covalent bonds may be carried out prior to depositing the at least one carbon sheet or after depositing the at least one carbon sheet. Functionalization with covalent bonds may also occur during operation of the electronic device, such as during the step of applying a voltage sweep to the device. In certain other embodiments, the electronic devices prepared by the process disclosed hereinabove further comprise chemically functionalizing the at least one carbon sheet with non-covalent bonds. Such functionalization with non-covalent bonds may be carried out prior to depositing the at least once carbon sheet or after depositing the at least one carbon sheet. Functionalization with non-covalent bonds may also occur during operation of the electronic devices, such as during the step of applying a voltage sweep to the device. In some embodiments, functionalization of the at least one carbon sheet may comprise adsorption of at least one molecule to the at least one carbon sheet, where the at least one molecule is adsorbed on the at least one carbon sheet. In other embodiments, functionalization of the at least one carbon sheet may comprise ionic bonding of at least one molecule to the at least one carbon sheet.

An exemplary but non-limiting embodiment of a two-terminal electronic device and a process for preparing the device is described below and illustrated in FIG. 4. In brief, a wafer of dielectric material 401, such as $SiO_2$, for example, is presented and a pattern 402 is made on wafer 401. In the embodiment presented, the pattern 402 is made with chromium metal. A protective layer 403 is then applied, coating the exposed dielectric material 401 and the pattern 402. In an embodiment, the protective layer comprises $Al_2O_3$ applied in about a 10 nm thick layer. In the generalized embodiment shown, the pattern 402 and the protective layer 403 overcoating 402 are removed, exposing a patterned surface of the dielectric material 401 following the removal process. A carbon sheet 404 is then deposited, overcoating the exposed dielectric material 401 and the protective layer 403. The carbon sheet 404 may comprise a discontinuous carbon layer in an embodiment. The carbon sheet 404 typically includes graphene or graphite. Removal of the remaining protective layer 403 and its overcoating carbon sheet 404 leaves behind a patterned at least one carbon sheet 405 on the dielectric material 401. Positioning electrode terminals 406 at each end of the patterned at least one carbon sheet 405 completes assembly of this embodiment of the electronic device. The electrode terminals 406 separately comprise a source electrode and a drain electrode. Applying a voltage sweep to the completed device in an embodiment may be used as a non-limiting means of monitoring performance of the electronic device, setting an initial device conduction state, or functionalizing the patterned at least one carbon sheet 405. All views shown in FIG. 4 are side views of the electronic device, with the exception of the final view where the electrode terminals 406 are attached, which is a top view.

Experimental Examples

The following experimental examples are included to demonstrate particular aspects of the present disclosure. It should be appreciated by those of skill in the art that the methods described in the examples that follow merely represent exemplary embodiments of the disclosure. Those of skill in the art should, in light of the present disclosure, appreciate that many changes can be made in the specific embodiments described and still obtain a like or similar result without departing from the spirit and scope of the present disclosure.

Unless stated otherwise below, all electrical property measurements were taken at room temperature under a vacuum of ~$5\times10^{-5}$ mm Hg. Electrical transport properties were measured using a Desert Cryogenics TT-probe 6 system. Current-voltage data were collected with an Agilent 4155C semiconductor parameter analyzer. For convenience and unless stated otherwise, the voltages and currents specified below refer to drain-source voltages and drain currents. High resolution TEM images were acquired with either a JEOL-2100F (accelerating voltage of 200 kV) or JEOL-300F (accelerating voltage of 300 kV) TEM instrument. SEM characterization was accomplished with a JEOL-6500 field emission SEM.

Example 1

C—$SiO_2$—SiC Nanocable Electronic Devices

Preparation of C—$SiO_2$SiC Nanocables:

C—$SiO_2$—SiC nanocables were prepared by a high temperature CVD process. As-synthesized C—$SiO_2$—SiC nanocables were several μm in length and about 20 nm to about 50 nm in diameter. The SiC nanowire core of each nanocable was comprised by a β-SiC single crystal. The middle $SiO_2$ dielectric layer was about 2 nm to about 5 nm in thickness. The outer carbon sheath was comprised by at least one graphene or graphite sheet or by multi-walled carbon nanotubes. Together, an assembly of multi-walled carbon nanotubes can be considered to comprise a defect-ridden graphene sheet wrapping the dielectric core of the nanocable.

Figure 5:
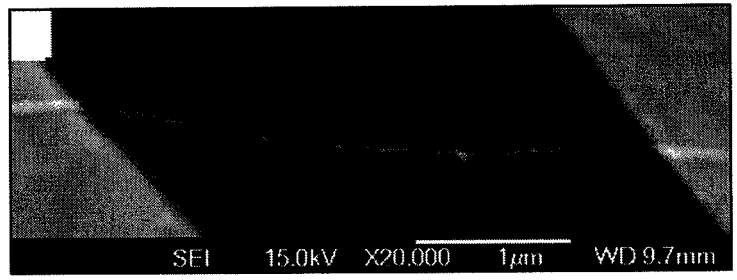
FIG. 5 shows a representative embodiment of an SEM image of a long channel C—$SiO_2$—SiC nanocable electronic device.
Figure 6:
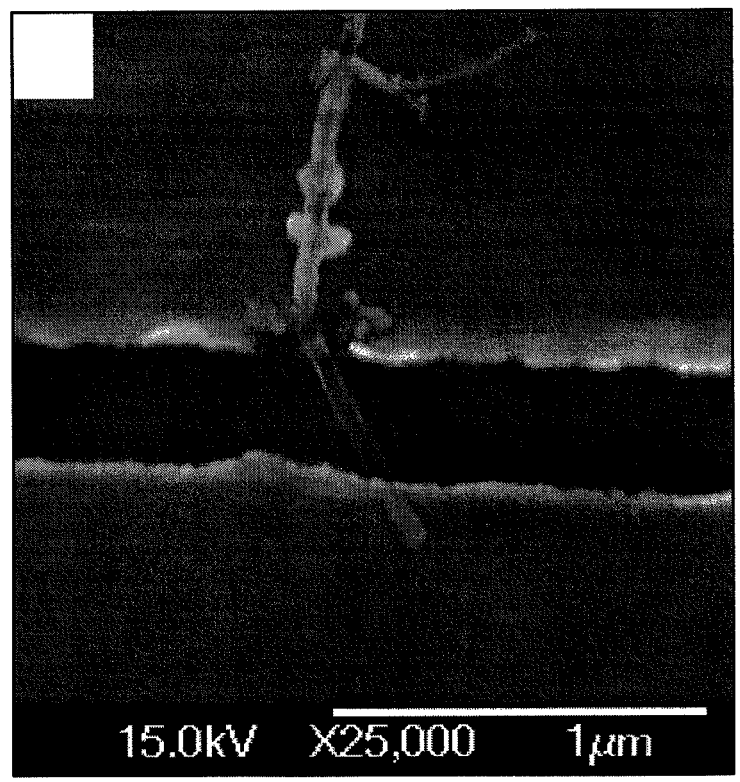
FIG. 6 shows a representative embodiment of an SEM image of a short channel C—$SiO_2$—SiC nanocable electronic device.

Characterization of Two-Terminal C—$SiO_2$SiC Nanocable Electronic Devices:

Each C—$SiO_2$—SiC nanocable-based two-terminal electronic device was prepared and characterized as follows. C—$SiO_2$—SiC nanocables were dispersed in ethyl alcohol with the aid of sonication and then deposited on the surface of $Si_3N_4$— or $SiO_2$-covered highly doped Si substrates via spin coating. The $Si_3N_4$ or $SiO_2$ dielectric layer was about 200 nm thick. Electrode terminals were then patterned over a deposited nanocable by either standard photolithography or electron-beam lithography techniques. Photolithography produced long channel devices (>1 μm separation between source and drain electrode terminals), and electron-beam lithography produced short channel electronic devices (<1 μm separation between source and drain electrode terminals). The electrode terminals were constructed from Pt and were about 100 nm thick for photolithography fabrication and about 50 nm thick for electron-beam lithography fabrication. After lift-off of photoresist, the nanocable electronic devices were characterized by SEM. A representative embodiment of an SEM image of a long channel C—$SiO_2$—SiC nanocable-based electronic device is shown in FIG. 5 and that of a short channel C—$SiO_2$—SiC nanocable-based electronic device is shown in FIG. 6. During SEM observation, only two-terminal electronic devices having a single nanocable bridging between the two electrode terminals were characterized.

Performance of Two-Terminal C—$SiO_2$SiC Nanocable Electronic Devices in the Presence of a Bias Voltage Sweep:

In the presence of a bias voltage sweep, the C—$SiO_2$—SiC nanocable devices exhibited BIV behavior and high PVRs, instead of a linear dependence of current on voltage. Representative results for different C—$SiO_2$—SiC nanocable channel lengths are shown in FIGS. 7 and 8.

Figure 7:
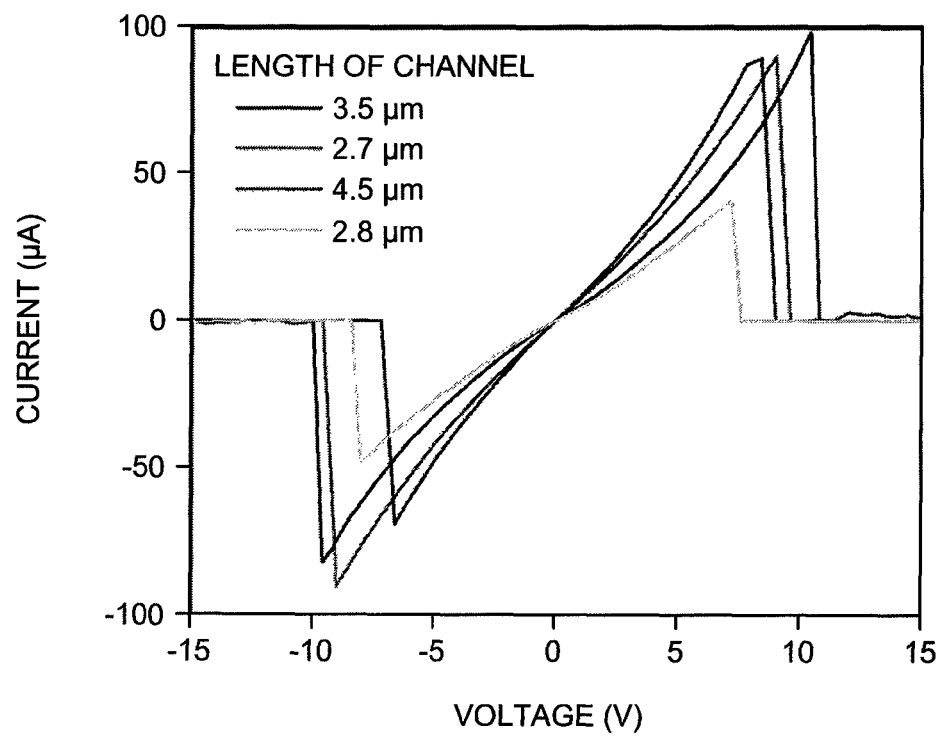
FIG. 7 shows embodiments of BIV behavior over a bias sweep range of −15 V to +15 V for various long channel C—$SiO_2$—SiC nanocable electronic devices.
Figure 8:
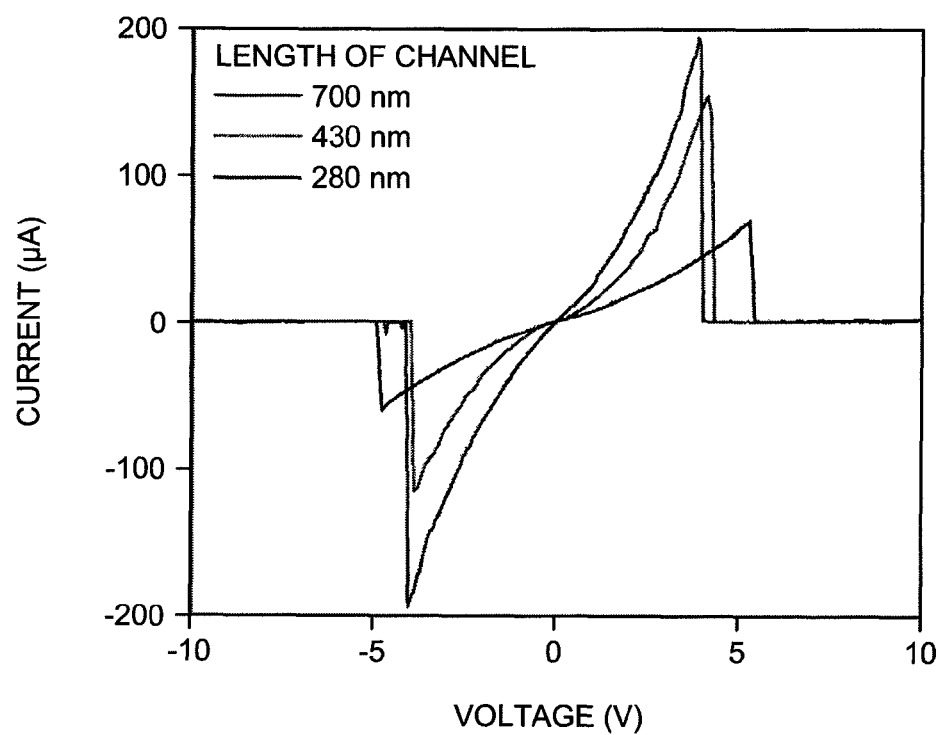
FIG. 8 shows embodiments of BIV behavior over a bias sweep range of −15 V to +15 V for various short channel C—$SiO_2$—SiC nanocable electronic devices.
Figure 9:
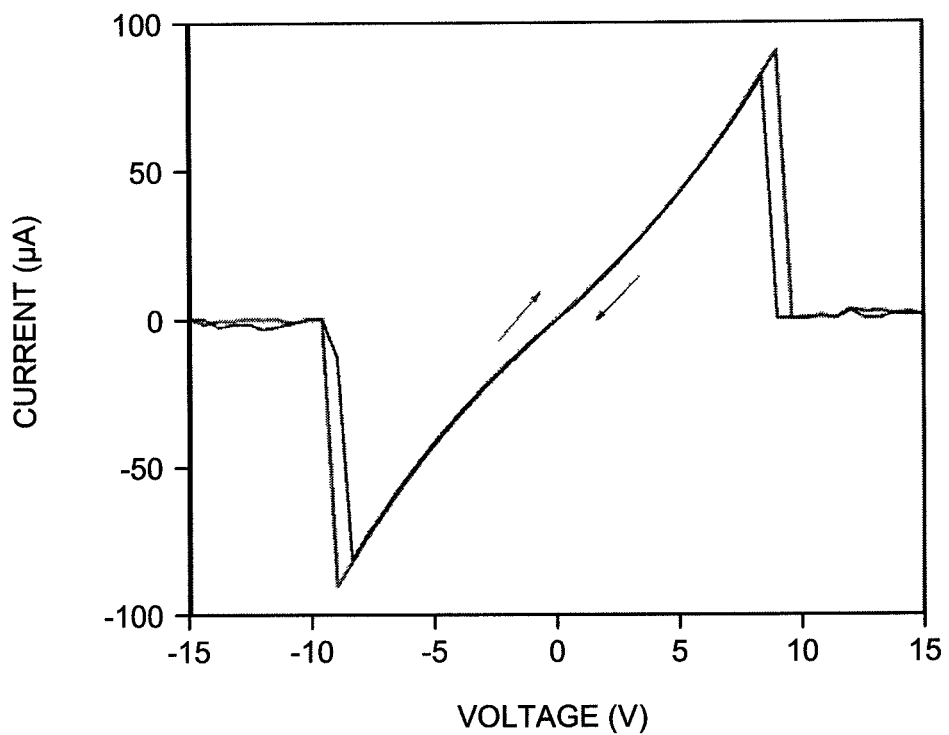
FIG. 9 shows an embodiment of a reverse bias sweep of +15 V to −15 V for a C—$SiO_2$—SiC nanocable device having a channel length of 2.7 µm.

Long-Channel C—$SiO_2$—SiC Nanocable Devices:

As shown in FIG. 7, over a voltage sweep width of −15 V to +15 V, a C—$SiO_2$—SiC nanocable device with a channel length of 3.5 μm remained in a low-conduction state at high negative bias until the current sharply increased at −9.6 V to a peak of 82 μA with a PVR of about 6000. The device then remained at a high-conduction state until the bias reached +10.4 V, where the current decreased from ~100 μA to <10 pA, resulting in a PVR of ~$1.7\times10^6$. The device remained in the low-conduction state while the voltage was increased to +15 V. Similarly, a C—$SiO_2$—SiC nanocable device with channel length of 2.7 μm exhibited BIV features at −9 V and +9 V, respectively. The PVR at +9 V was ~$1.3\times10^4$. As shown in FIG. 9, reversing the bias sweep from +15 V to −15 V for this C—$SiO_2$—SiC nanocable device produced almost the same trace of the current-voltage curve, except that the BIV $V_{th}$ occurred at a slightly lower bias of ±8.4 V. Another C—$SiO_2$—SiC nanocable electronic device with a channel length of 2.8 μm displayed BIV behavior at −8 V and +7.2 V with a PVR about 6700. BIV was found on another C—$SiO_2$—SiC nanocable electronic device with a channel length of 4.5 μm, producing $V_{th}$ values at −6.6 V and +8.4 V. The PVR was ~2800 at −6.6 V and $4.7\times10^5$ at +8.4 V in this device. Repeatable BIV behavior was observed on more than 20 different long-channel nanocable devices with $V_{th}$ absolute values typically in the range of 6-12 V range and PVRs in the range of $10^3$-$10^6$.

Short Channel C—$SiO_2$SiC Nanocable Devices:

When the nanocable channel was shortened to below about 1 μm, the two-terminal C—$SiO_2$—SiC nanocable electronic devices exhibited BIV behavior with lower $V_{th}$. As shown in FIG. 8, a C—$SiO_2$—SiC nanocable electronic device with a channel length of 700 nm had BIV behavior at +5.2 V and −4.8 V with PVRs of 6500 and 2400, respectively. A C—$SiO_2$—SiC nanocable electronic device having a channel length of 430 nm exhibited BIV behavior at +4.2 V and −4.0 V with PVRs of 7100 and 86000, respectively. Another C—$SiO_2$—SiC nanocable electronic device having a channel length of 280 nm displayed BIV behavior at +3.9 V and −4.0 V with PVRs of 3000 and 1300, respectively, during a bias sweep from −5 V to +5 V. Based on the above results, the short channel C—$SiO_2$—SiC nanocable electronic devices have lower BIV $V_{th}$ than do the long channel C—$SiO_2$—SiC nanocable devices, although the BIV $V_{th}$ is not directly proportional to channel length. A summary of the dependence of $V_{th}$ and PVR on C—$SiO_2$—SiC nanocable channel length is presented in Table 1.

Figure 10:
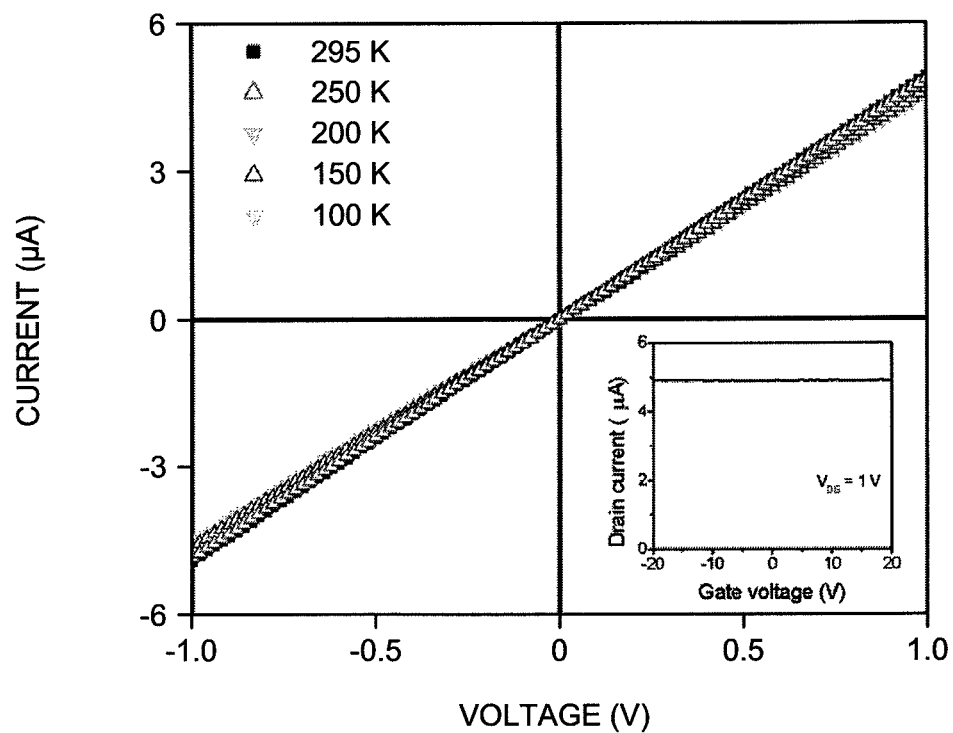
FIG. 10 shows an embodiment of variable temperature conductance of C—$SiO_2$—SiC nanocable devices over a temperature range of 100 K to 295 K and a bias voltage sweep of −1 V to +1 V.

Temperature Dependence of BIV Behavior in C—$SiO_2$—SiC Nanocable Electronic Devices:

The C—$SiO_2$—SiC nanocable devices showed high current flow at low bias (from a few μA to several hundred μA at 1 V). The conductances of the nanocables were almost independent of gate voltages, where a highly-doped Si substrate was used as the back gate. To determine the nature of electrical transport for the C—$SiO_2$—SiC nanocable devices, temperature dependent current-voltage profiles were obtained for several devices. The temperatures for these measurements ranged from room temperature (295 K) to about 100 K. The variable temperature conductance results showed little temperature effect on the electrical transport behavior of C—$SiO_2$—SiC nanocable devices, as shown in FIG. 10. The relatively invariant temperature behavior demonstrated in FIG. 10 is characteristic of graphene and metallic carbon nanotubes.

Example 2

ON/OFF Bias Switching of C—$SiO_2$—SiC Nanocable Electronic Devices

Figure 11:
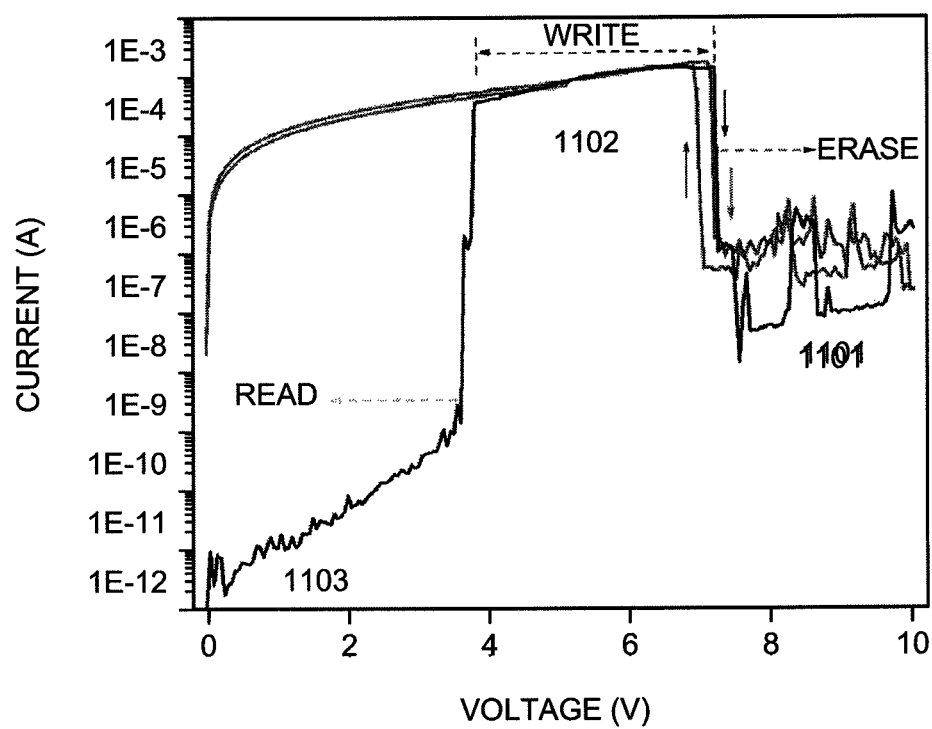
FIG. 11 shows an embodiment of a repetitive bias voltage sweep of a C—$SiO_2$—SiC nanocable electronic device.

The two-terminal C—$SiO_2$—SiC nanocable devices can be directly used for fast switching based on their BIV with high PVRs. To achieve an OFF state, the devices are operated at a relatively high reading bias (higher than $V_{th}$). The nanocable electronic devices show distinct high- and low-conduction states under different bias sweeping protocols. As revealed in FIG. 11, when a two-direction bias sweep (from 0 V to 10 V and then back to 0 V) was applied to a C—$SiO_2$—SiC nanocable electronic device, the device exhibited BIV behavior similar to that described above for a one-direction bias sweep. Except for the first-time sweeping, the device was in a low-conduction state at a bias below 3.6 V, in a high-conduction state at a bias between 3.8-7.1 V, and in an intermediate but relatively low conduction state at a bias higher than 7.1 V. Based on this bistable conduction feature, the two-terminal C—$SiO_2$—SiC nanocable devices can be used in switching and memory applications. For example, a bias pulse higher than 7.1 V (for instance, 8 V) can be used as the erase bias 1101; a bias between 3.8-7.1 V (for instance, 4 V) can be used as the write bias 1102; and the low-conduction state and high-conduction state can be read at the same low-bias (for instance, 1 V) 1103.

Figure 12A:
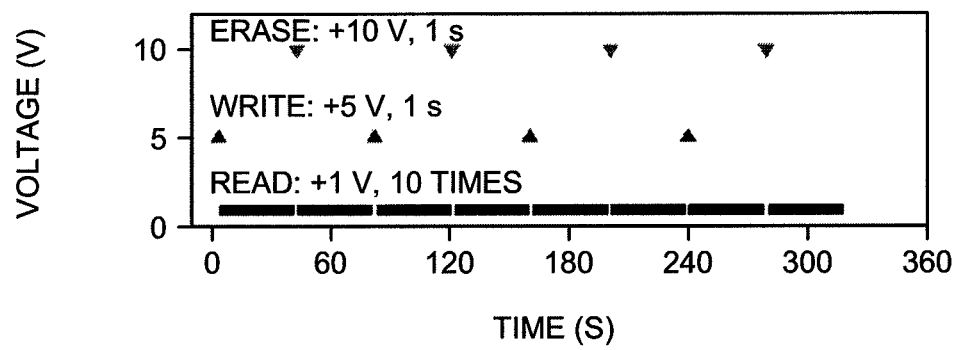
FIG. 12 shows an embodiment of the memory performance of a long channel C—SiO$_2$—SiC nanocable electronic device having a channel length of 2.8 μm, as obtained from a +5 V write bias pulse for 1 s and +10 V erase bias pulse for 1 s.
Figure 12B:
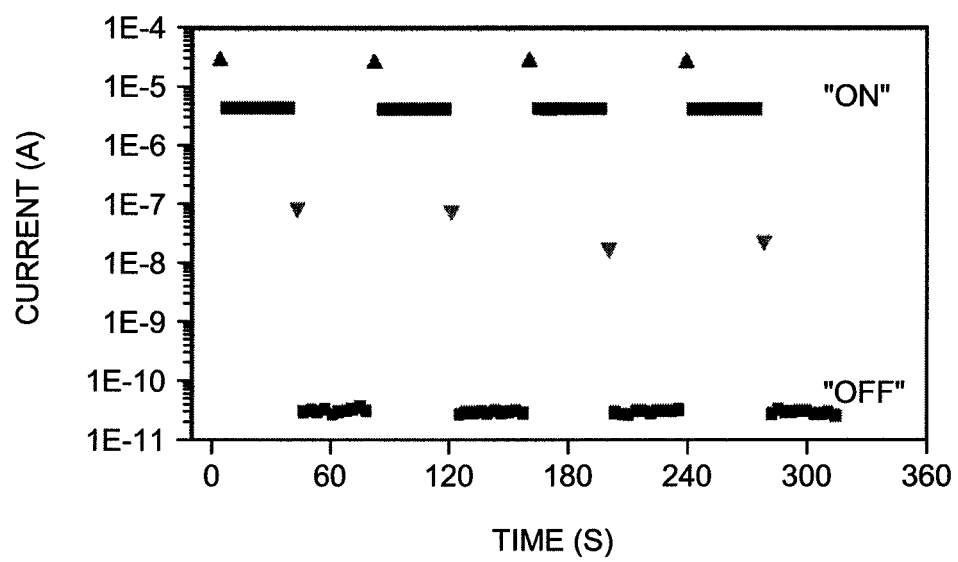
Figure 13A:
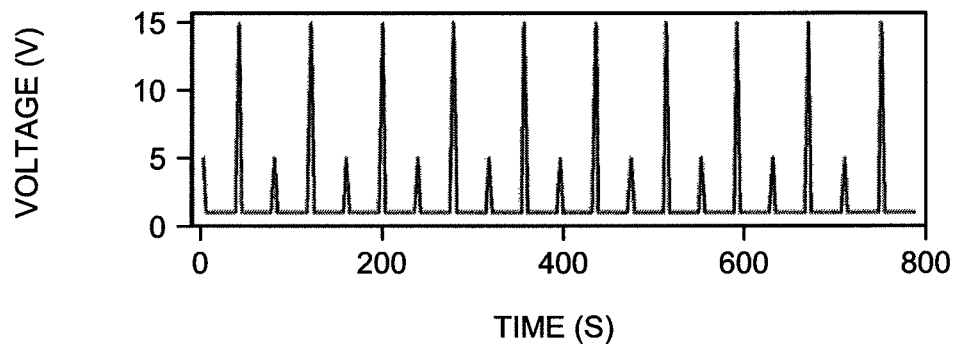
FIG. 13 shows an embodiment of the memory performance of a long channel C—SiO$_2$—SiC nanocable electronic device having a channel length of 4.5 μm, as obtained from a +5 V write bias pulse for 1 s and +15 V erase bias pulse for 1 s.
Figure 13B:
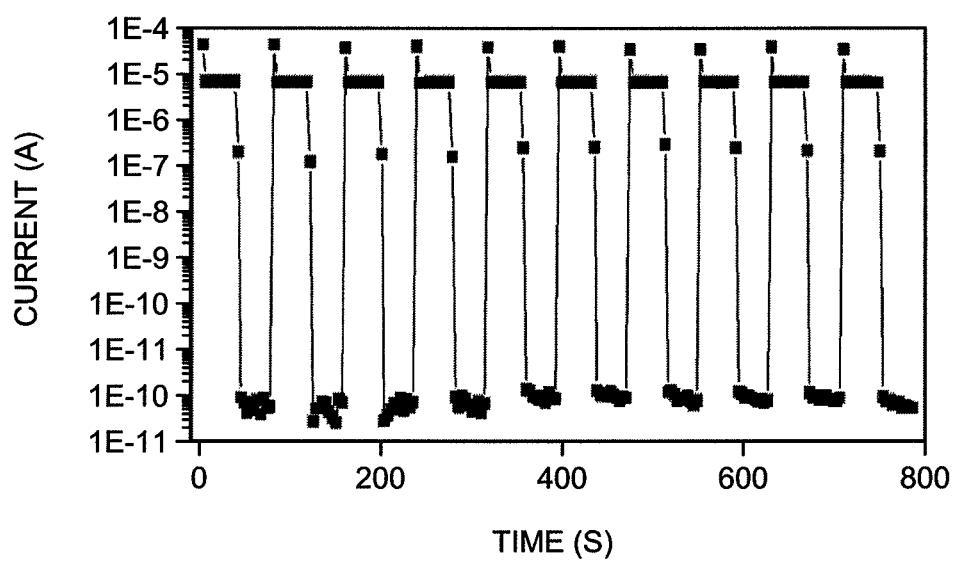
Figure 14:
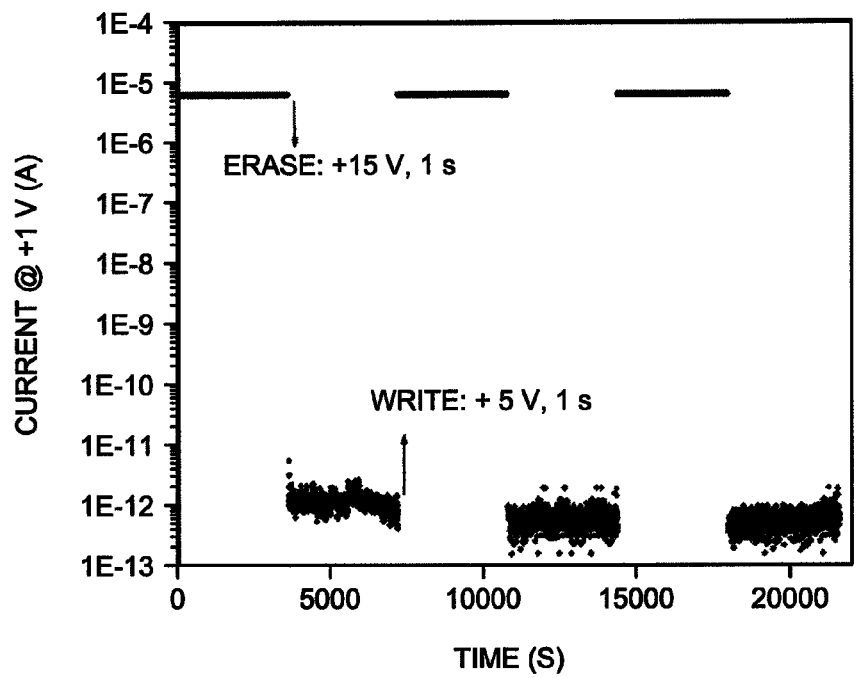
FIG. 14 shows an embodiment of the long term memory reading performance of a long channel C—SiO$_2$—SiC nanocable electronic device having a channel length of 4.5 μm, as obtained from a +5 V write bias pulse for 1 s and +15 V erase bias pulse for 1 s, followed by 1000 consecutive current reads at +1 V.

Memory Performance of Lone Channel C—$SiO_2$—SiC Nanocable Devices:

The memory performance of a C—$SiO_2$—SiC nanocable electronic device having a long channel length of 2.8 μm is shown in FIG. 12. As demonstrated in Example 1 above, this device exhibited BIV behavior at −8 V and +7.2 V with a PVR about 6700 for both $V_{th}$. The ON/OFF memory states for this device could be switched by a +5 V write bias pulse for 1 s and +10 V erase bias pulse for 1 s, with an ON/OFF ratio of about $1.4 \times 10^5$. After each write/erase operation, the deive current was read ten times consecutively at +1 V. Additional long channel C—$SiO_2$—SiC nanocable device memory performance curves are presented in FIGS. 13 and 14. FIG. 13 shows the performance of a long channel C—$SiO_2$—SiC nanocable device having a channel length of 4.5 μm. A pulse of +5 V for 1 s turns the device to the high-conduction ON state, and a +15 V pulse for 1 s changes the device to a low-conduction OFF state. FIG. 14 shows long term room-temperature memory reading performance of the C—$SiO_2$—SiC nanocable device shown in FIG. 13. After each write/erase operation, the current of the device was consecutively read at +1 V for 1000 times, in contrast to the shorter read times employed in FIG. 13.

Figure 15:
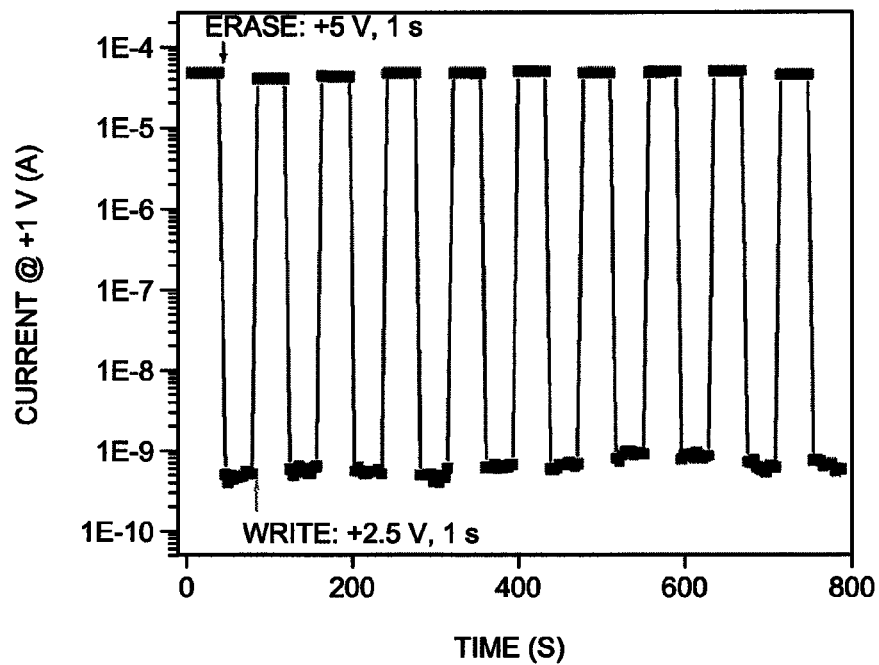
FIG. 15 shows an embodiment of the memory reading performance of a short channel C—SiO$_2$—SiC nanocable electronic device having a channel length of 280 nm, as obtained from a +2.5 V write bias pulse for 1 s and +5 V erase bias pulse for 1 s, followed by 10 consecutive current reads at +1 V.
Figure 16:
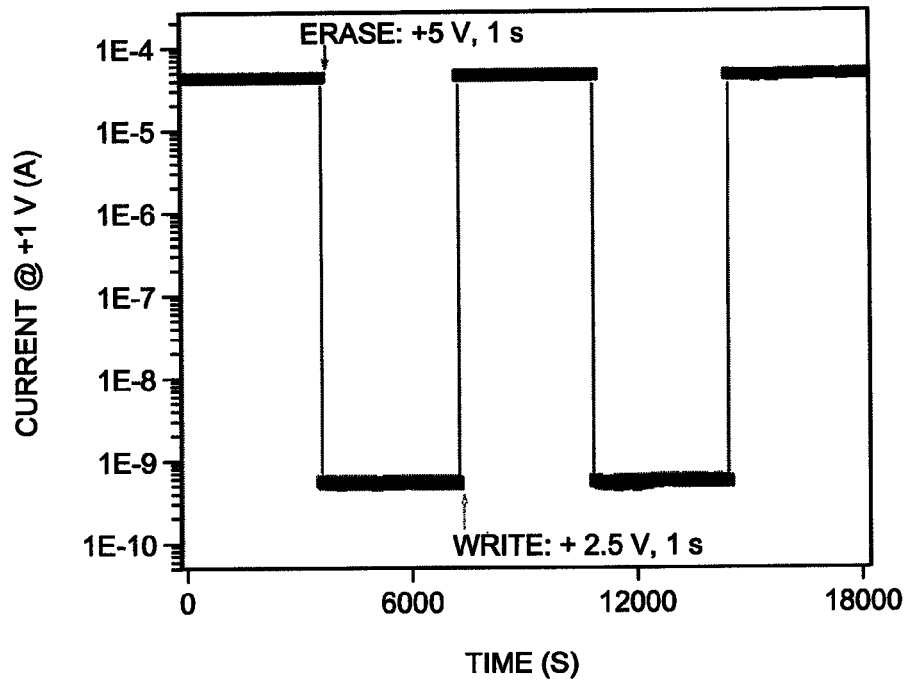
FIG. 16 shows an embodiment of the long term memory reading performance of a short channel C—SiO$_2$—SiC nanocable electronic device having a channel length of 280 nm, as obtained from a +2.5 V write bias pulse for 1 s and +5 V erase bias pulse for 1 s, followed by 1000 consecutive current reads at +1 V.

Memory Performance of Short Channel C—$SiO_2$SiC Nanocable Devices:

Due to the lower BIV $V_{th}$ exhibited in the short channel C—$SiO_2$—SiC nanocable devices, a lower write/erase bias was generally needed for these devices to serve as memory. The memory performance of a C—$SiO_2$—SiC nanocable device having a channel length of 280 nm is shown in FIGS. 15 and 16. In each Figure, bias voltages of +2.5 V and +5 V were used as the write bias and erase bias, respectively. After each write/erase pulse for 1 s, the drain currents were consecutively read for 10 times (FIG. 15) or 1000 times (FIG. 16) at +1 V. The long term measurements indicated an ON/OFF ratio greater than $5.6 \times 10^4$, which was similar to that obtained for the analogous short term read (FIG. 15). This test demonstrated memory stability of the two-terminal C—$SiO_2$—SiC nanocable over the test lifetime.

Figure 17:
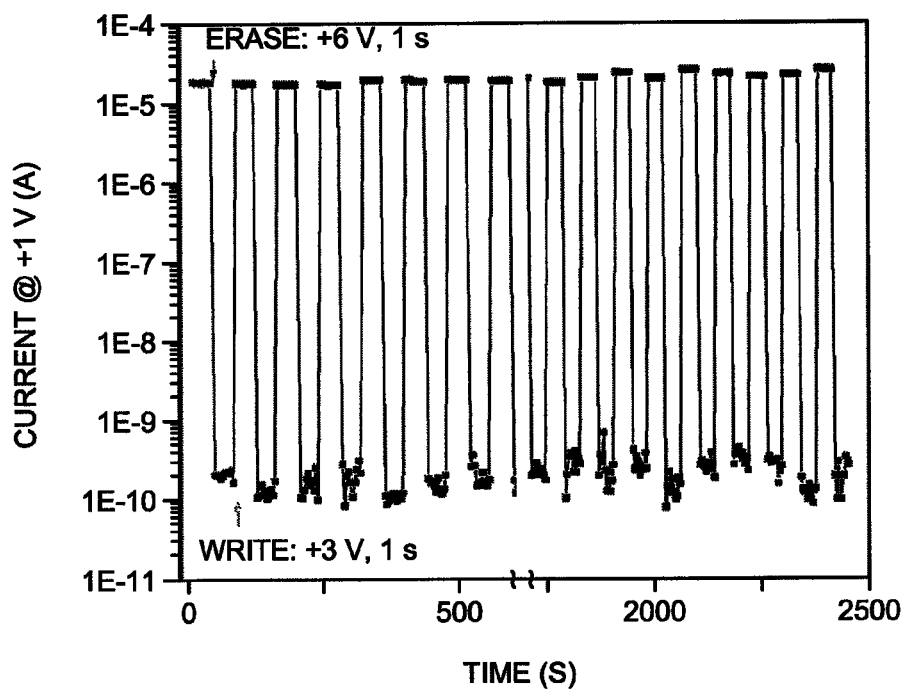
FIG. 17 shows an embodiment of the memory reading performance of a short channel C—SiO$_2$—SiC nanocable electronic device having a channel length of 430 nm, as obtained from a +3 V write bias pulse and a +6 V erase bias pulse.
Figure 18:
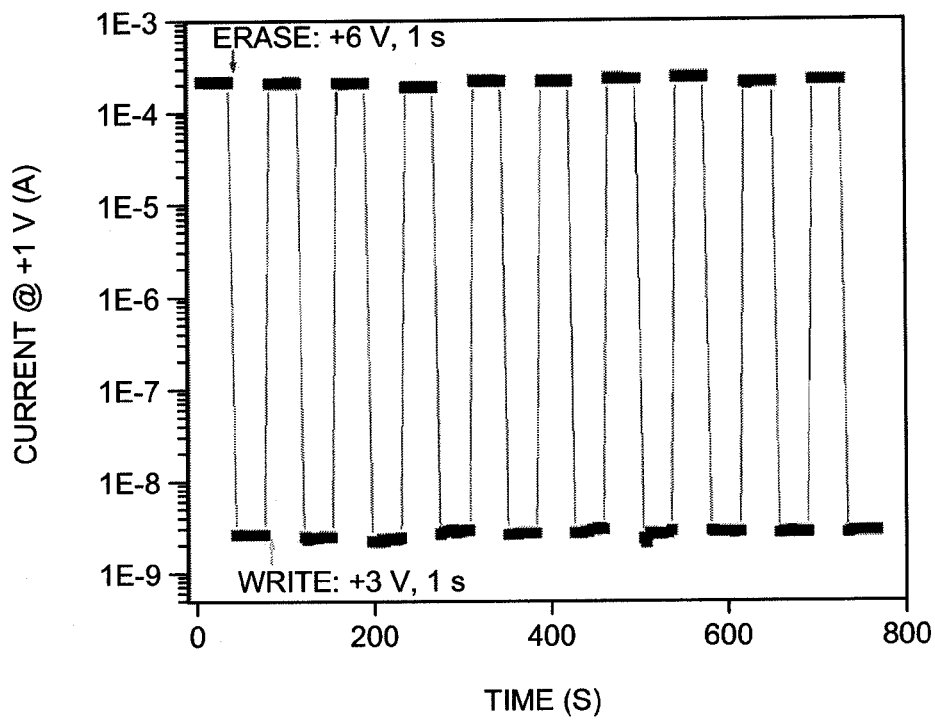
FIG. 18 shows an embodiment of the memory reading performance of a short channel C—SiO$_2$—SiC nanocable electronic device having a channel length of 360 nm, as obtained from a +3 V write bias pulse and a +6 V erase bias pulse.
Figure 19:
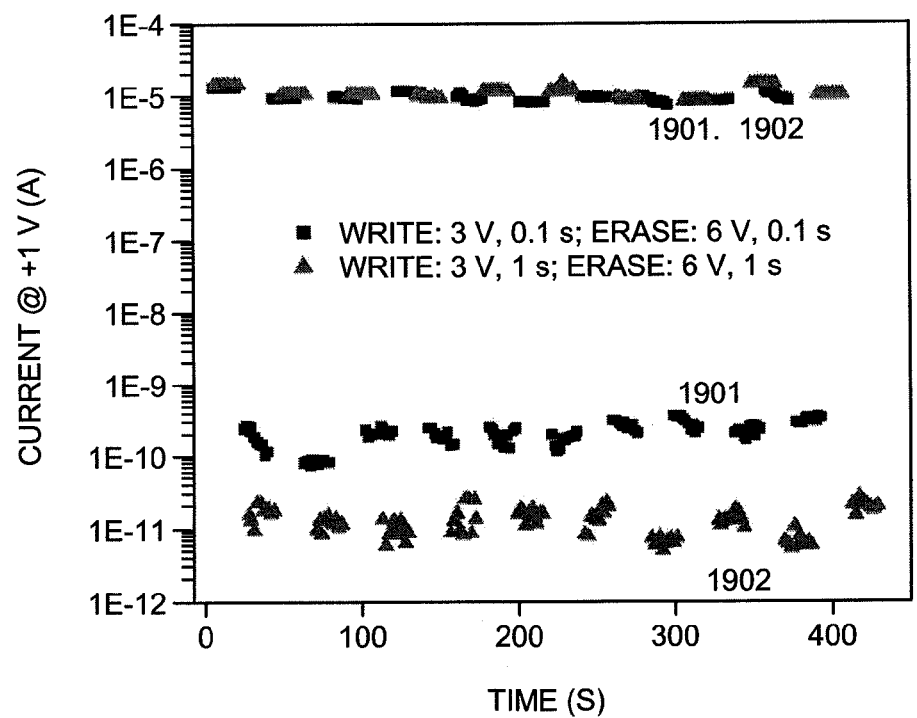
FIG. 19 shows embodiments of the memory reading performance of a short channel C—SiO$_2$—SiC nanocable electronic device having a channel length of 700 nm, as obtained from a +3 V write bias pulse and a +6 V erase bias pulse, with a write/erase bias pulse times of either 0.1 or 1 second.

Memory performance testing for additional short channel nanocable devices are presented in FIGS. 17-19. The multi-cycle memory performance of a C—$SiO_2$—SiC nanocable device having a channel length of 430 nm is presented in FIG. 17. The memory conduction states in this device were switched by a +3 V write bias pulse and a +6 V erase bias pulse. The ON/OFF ratio of memory was higher than $5 \times 10^4$. FIG. 18 shows the memory performance of a C—$SiO_2$—SiC nanocable device having a channel length of 360 nm. This device exhibited BIV behavior at −4.4 V and +4.9 V, with respective PVRs of 12200 and 7100. With a write bias voltage of +3 V and an erase bias voltage of +6 V, the device exhibited an ON/OFF ratio greater than $6.0 \times 10^4$. FIG. 19 shows the memory performance of a C—$SiO_2$—SiC nanocable device having a channel length of 700 nm. The BIV behavior of this device was previously presented in FIG. 8. In FIG. 19, two different pulse times (0.1 or 1 second) were used to turn the memory ON with a +3 V write bias pulse or OFF with a +6 V erase bias pulse. The results in FIG. 19 showed that the shorter erasing pulse operation resulted in a higher OFF current, possibly due to an incomplete depletion process. In contrast, the ON currents did not show a clear difference. This result likely reveals that electron tunneling from C to SiC is faster than that from SiC to C.

Example 3

C—$SiO_2$—Si and C—$SiO_2$ Nanocable Electronic Devices

Two-terminal electronic devices built with C—$SiO_2$—Si or C—$SiO_2$ nanocables were fabricated and tested for comparison to the C—$SiO_2$—SiC nanocable electronic devices described above. These devices were constructed as follows.

Figure 20:
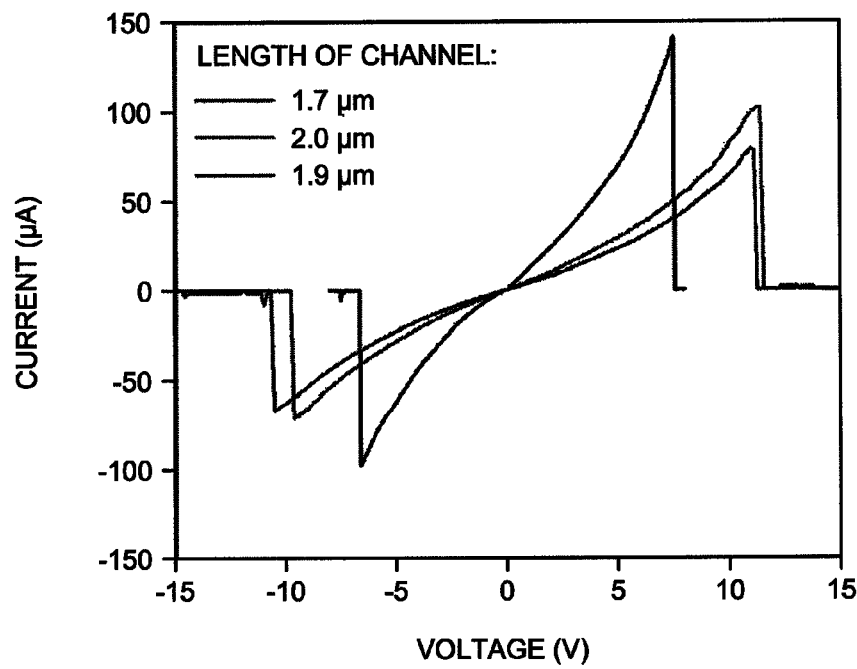
FIG. 20 shows embodiments of BIV behavior over a bias sweep range of −15 V to +15 V for various C—SiO$_2$—Si nanocable electronic devices.

Preparation of C—$SiO_2$—Si and C—$SiO_2$ Nanocables:

Single-crystal intrinsic silicon nanowires (SiNWs) were prepared by an Au-catalyzed CVD method in which $SiCl_4$ was used as the Si source. A 5 nm Au thin film on a Si(100) substrate was used as the catalyst. Catalytic growth of SiNWs occurred upon introducing a mixture of $SiCl_4$, $H_2$ and Ar gases to the catalyst at 850° C. The as-synthesized SiNWs were 50-120 nm in diameter. To synthesize nanocables, the SiNWs were etched in 10% HF etchant for 5 min to completely remove native oxide. The SiNWs were then dry oxidized in air at 850° C. for 15 min to form a thin layer of $SiO_2$ approximately 5 nm in thickness for use in forming C—SiO$_2$—Si nanocables. Oxidation at 1050° C. for 2 hours to produced SiO$_2$ nanowires for use in forming C—SiO$_2$ nanocables. A graphitic C layer was coated on the outer surface of SiO$_2$—Si nanowires or SiO$_2$ nanowires by the thermal decomposition of C$_2$H$_2$, diluted with H$_2$, at 900° C. for 3 min in a tube furnace. Two-terminal nanocable devices were thereafter fabricated using a similar photolithography route as described hereinabove for C—SiO$_2$—SiC nanocable devices Performance of Two-Terminal C—SiO$_2$—Si Nanocable Electronic Devices in the Presence of a Bias Voltage Sweep:

Electrical property measurements showed that two-terminal C—SiO$_2$—Si nanocable devices exhibited BIV properties similar to those observed for the C—SiO$_2$—SiC nanocable devices described hereinabove. As shown in FIG. 20, a C—SiO$_2$—Si nanocable device having a channel length of 1.7 μm and a nanocable diameter of 110 nm showed typical BIV characteristics. The negative bias V$_{th}$ of the device was −6.6 V and the positive bias V$_{th}$ was +7.5 V, with PVRs of 2900 and 9700, respectively. Also shown in FIG. 20, a C—SiO$_2$—Si nanocable device having a channel length of 1.9 μm showed a negative bias V$_{th}$ of −10.5 V and a positive bias V$_{th}$ of +11.1 V, with PVRs of 1700 and 2100, respectively. Also shown in FIG. 20, a C—SiO$_2$—Si nanocable device with a channel length of 2.0 μm showed a negative bias V$_{th}$ of −9.6 V and a positive bias V$_{th}$ of +11.4 V, with PVRs of 1000 and 1100, respectively.

Figure 21:
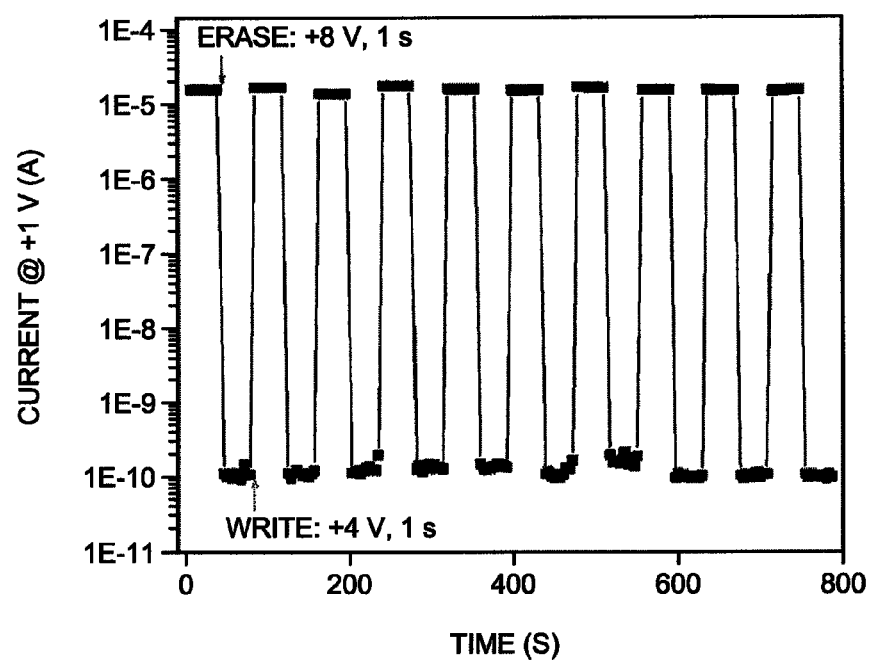
FIG. 21 shows an embodiment of the memory reading performance of a C—SiO$_2$—Si nanocable electronic device, as obtained from a +4 V write bias pulse for 1 second and a +8 V erase bias pulse for 1 second.

Memory Performance of Two-Terminal C—SiO$_2$—Si Nanocable Electronic Devices:

As shown in FIG. 21, the C—SiO$_2$—Si nanocable devices showed bistable memory switching behavior similar to that observed for the C—SiO$_2$—SiC nanocable devices. In the embodiment shown in FIG. 21, the C—SiO$_2$—Si two-terminal nanocable memory was turned ON by a pulse of +4 V for 1 s and turned OFF by a pulse of +8 V for 1 s, leading to an ON/OFF ratio higher than 1×10$^5$.

Figure 22:
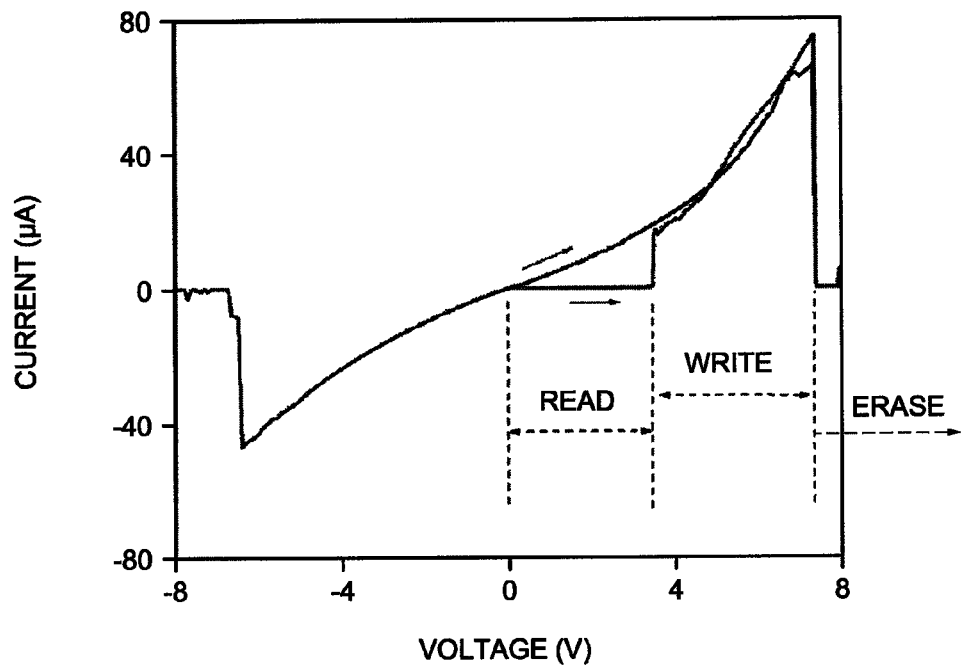
FIG. 22 shows an embodiment of BIV behavior over a bias sweep range of −8 V to +8 V for a C—SiO$_2$ nanocable electronic device having a channel length of 2.7 μm.
Figure 23:
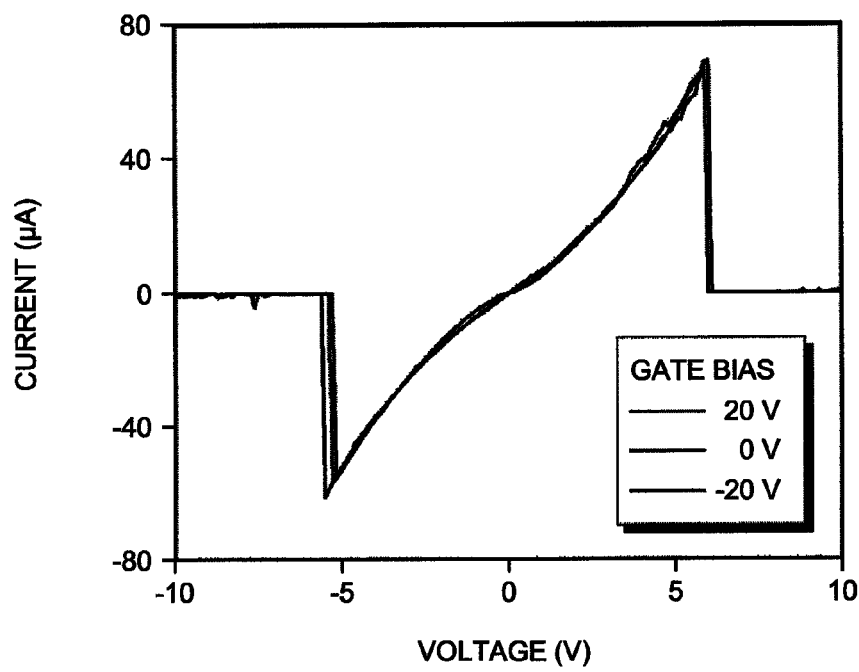
FIG. 23 shows an embodiment of BIV behavior over a bias sweep range of −10 V to +10 V for a C—SiO$_2$ nanocable electronic device having a channel length of 2.5 μm, as conducted in the presence of −20, 0, and +20 V gate biases.
Figure 24:
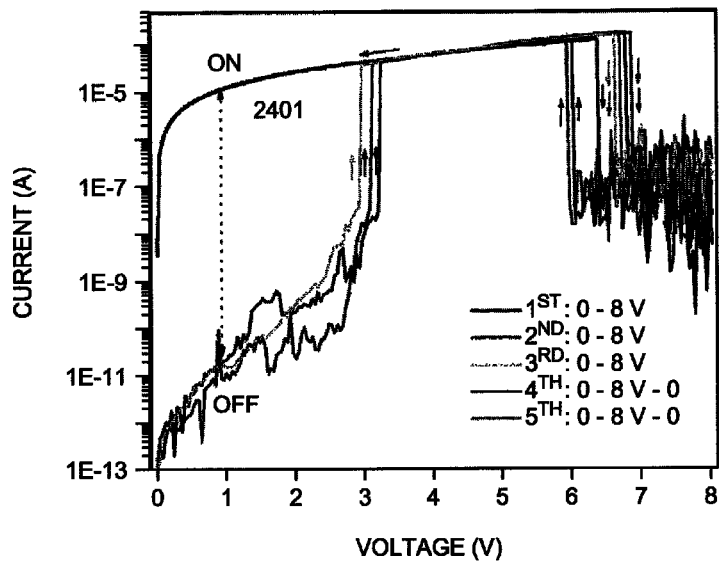
FIG. 24 shows an embodiment of a five-cycle bias sweep sequence from 0 to +8 V for a C—SiO$_2$ nanocable electronic device having a channel length of 2.4 μm.

Performance of Two-Terminal C—SiO$_2$ Nanocable Electronic Devices in the Presence of a Bias Voltage Sweep:

BIV behavior was also exhibited by two-terminal C—SiO$_2$ nanocable devices. As displayed in FIG. 22, a C—SiO$_2$ nanocable device with a channel length of 2.6 μm showed typical BIV behavior with a negative bias V$_{th}$ of −6.5 V and a positive bias V$_{th}$ of +7.3 V. FIG. 23 shows the BIV behavior of another C—SiO$_2$ nanocable device with a 2.5 μm channel length and nanocable diameter of 110 nm. The negative bias V$_{th}$ for this device was −5.5 V, and the positive bias V$_{th}$ was 6.0 V. The PVR was 1.15×10$^5$. In FIG. 23, a gate bias was set at −20, 0, or +20 V, although application of a gate bias did little to influence the C—SiO$_2$ nanocable device performance. For the gate bias analyses presented in FIG. 23, the Si substrate of the device served as the gate electrode. FIG. 24 shows a bias sweeping sequence for another C—SiO$_2$ nanocable device having a channel length of 2.4 μm over 5 bias sweep cycles.

The detailed pulse sequence presented in FIG. 24 follows: During the first bias sweep from 0 V to 8 V (2401), the C—SiO$_2$ nanocable device first remained in a high-conduction state at low bias, but the current sharply decreased from a peak of 125 μA at 6.35 V to a valley of 16.5 nA at 6.4 V, exhibiting a PVR of about 7500. The device then remained at a low-conduction state as the bias was increased to 8 V. Subsequent bias sweeps from 0 V to 8 V followed different current-voltage curves. During the second bias sweep from 0 to 8 V, the device first remained in a low-conduction state at low bias, but the current sharply jumped from 37.5 nA at 3.06 V to 41.2 μA at 3.12 V. The device remained in the high-conduction state until the bias increased to 6.84 V, where the current sharply decreased from a peak of 171 μA to a valley of 33 nA at 6.88 V, exhibiting a PVR of about 5200. The device then remained in a low-conduction state as the bias was increased to 8 V, exhibiting similar behavior to that observed during the first sweep. A third bias sweep from 0 V to 8 V produced a similar current-voltage curve. The reverse bias sweep from 8 V to 0 V followed the forward bias sweep from 0 V to 8 V, and the device regained its high-conduction state during the reverse sweep. With the forward bias sweeping, the device remained in its low-conduction state at low-bias until the bias increased to 3.19 V, where the current jumped from 25 nA to 41 μA at 3.24 V. The device remained in its high-conduction state when the bias was increased from 3.24 V to 6.76 V. When the bias was slightly higher than 6.76 V, the current sharply decreased from 172 μA at 6.76 V to 10 nA at 6.95 V, and the device remained in a low-conduction state. During the reverse sweep, the device stayed in its low-conduction state until the bias reached 6.04 V where the current jumped from 26 nA to 118 μA at 5.99 V. Then the device remained in its high-conduction state when the bias decreased to 0 V.

Figure 25:
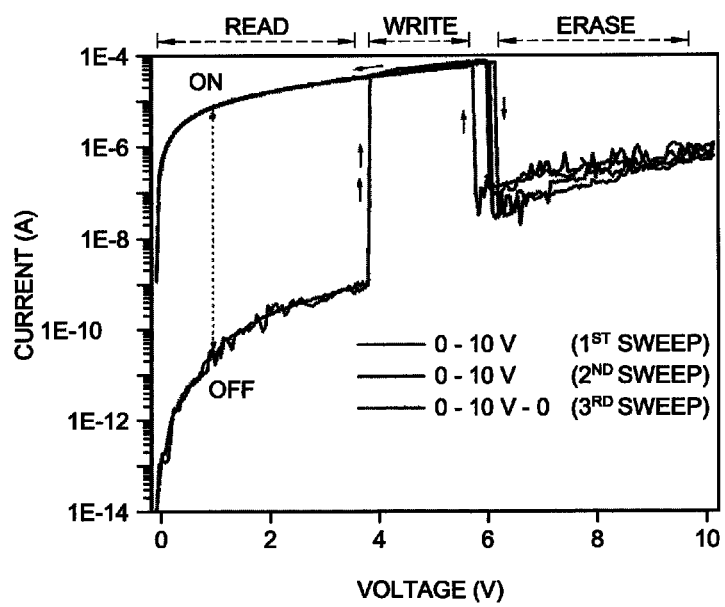
FIG. 25 shows an embodiment of a three-cycle bias sweep sequence from 0 to +10 V for a C—SiO$_2$ nanocable electronic device having a channel length of 2.5 μm and a nanocable diameter of 110 nm.
Figure 26A:
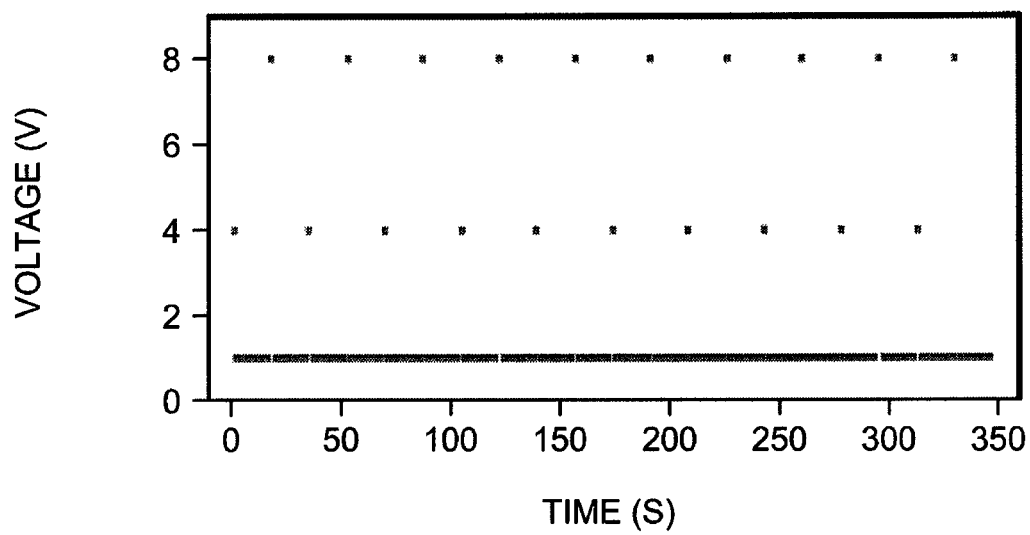
FIG. 26 shows an embodiment of the memory reading performance of a C—SiO$_2$ nanocable electronic device having a channel length of 2.5 μm and a nanocable diameter of 110 nm, as conducted with a +4 V write bias pulse for 1 ms and a +8 V erase bias pulse for 1 ms, each write/erase operation being followed by reading 10 consecutive times at +1 V.
Figure 26B:
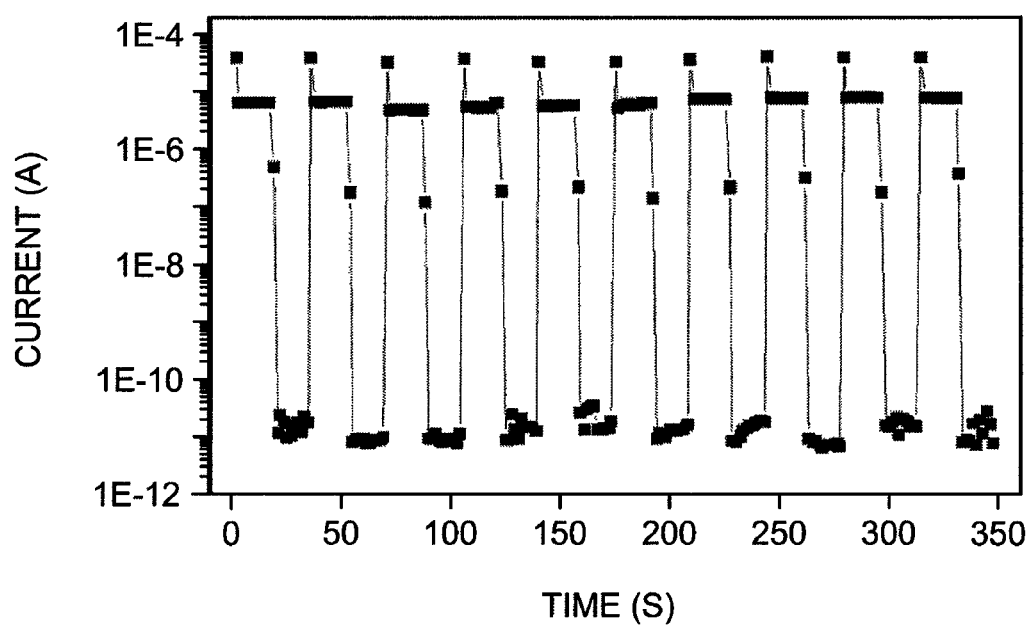

Memory Performance of Two-Terminal Nanocable Electronic Devices:

C—SiO$_2$ nanocable electronic devices also show bistable memory switching behavior. FIG. 25 demonstrates the BIV read/write performance of a C—SiO$_2$ nanocable device having a channel length of 2.5 μm and a nanocable diameter of 110 nm. FIG. 26 shows the bistable memory switching performance of the same device switched to the high-conductance ON state with a pulse of +4 V and the low conductance OFF state with a pulse of +8 V, each pulse being conducted for 1 ms. After each write-erase operation, the device was read consecutively at +1 V ten times. For the C—SiO$_2$ nanocable device presented in FIG. 26, the average ON/OFF ratio of this device is 4.6×10$^5$.

Figure 27:
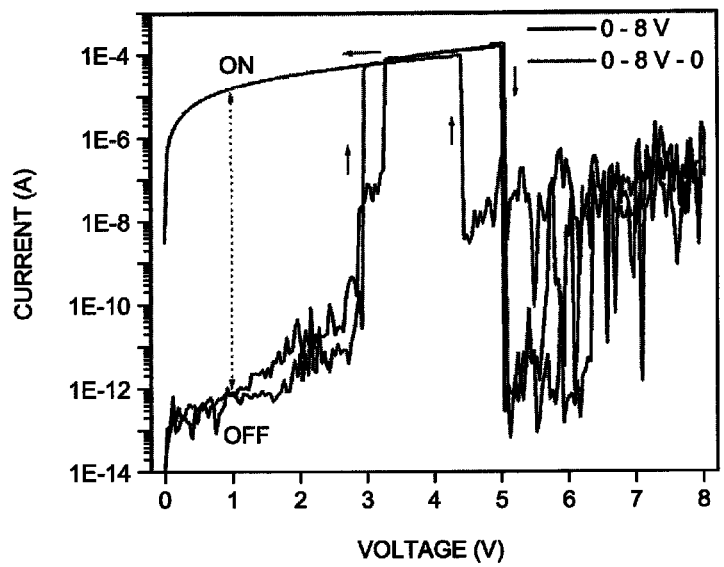
FIG. 27 shows an embodiment of a two-cycle bias sweep sequence from 0 to +8 V for a C—SiO$_2$ nanocable electronic device having a channel length of 1.9 μm and a nanocable diameter of 110 nm.
Figure 28:
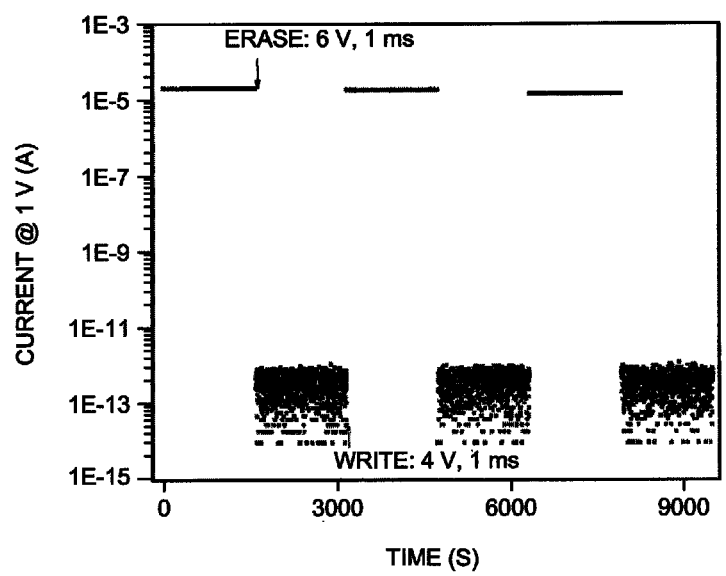
FIG. 28 shows an embodiment of the memory reading performance of a C—SiO$_2$ nanocable electronic device having a channel length of 1.9 μm and a nanocable diameter of 110 nm, as conducted with a +4 V write bias pulse for 1 ms and a +6 V erase bias pulse for 1 ms, each write/erase operation being followed by reading 1000 consecutive times at +1 V.

FIG. 27 presents the BIV read/write performance of another C—SiO$_2$ nanocable device having a channel length of 1.9 μm and a nanocable diameter of 110 nm. As presented in FIG. 28, a pulse of +4 V for 1 ms turns the device to the high-conduction ON state, and a pulse of +6 V for 1 ms returns the device to the low conduction OFF state. After each write/erase operation, the device current was read consecutively at +1 V 1000 times. The average ON/OFF ratio was 4.4×10$^7$.

Figure 29:
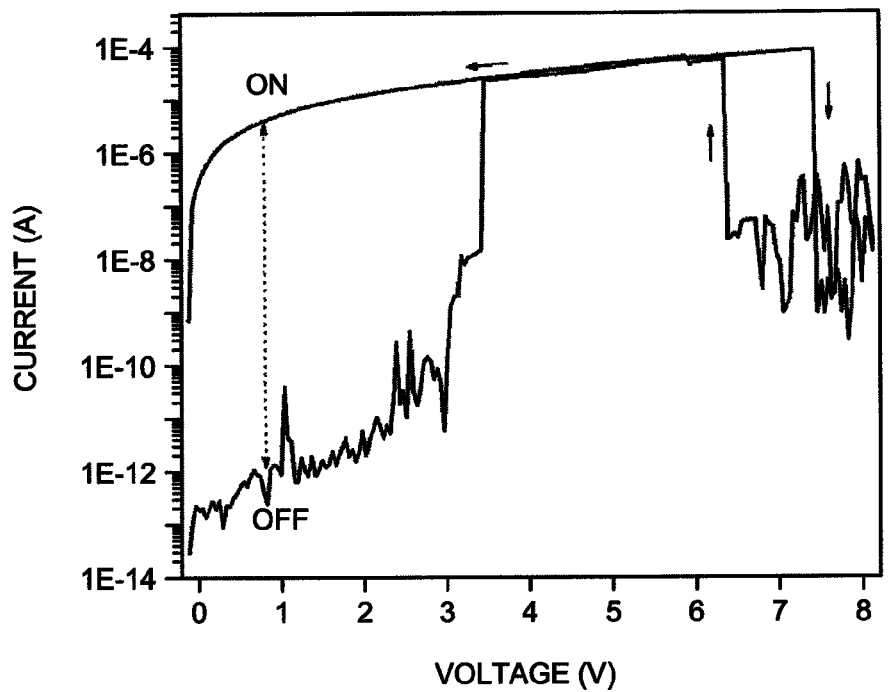
FIG. 29 shows an embodiment of a one-cycle read/write bias sweep sequence from 0 to +8 V for a C—SiO$_2$ nanocable electronic device having a channel length of 2.6 μm and a nanocable diameter of 140 nm.
Figure 30:
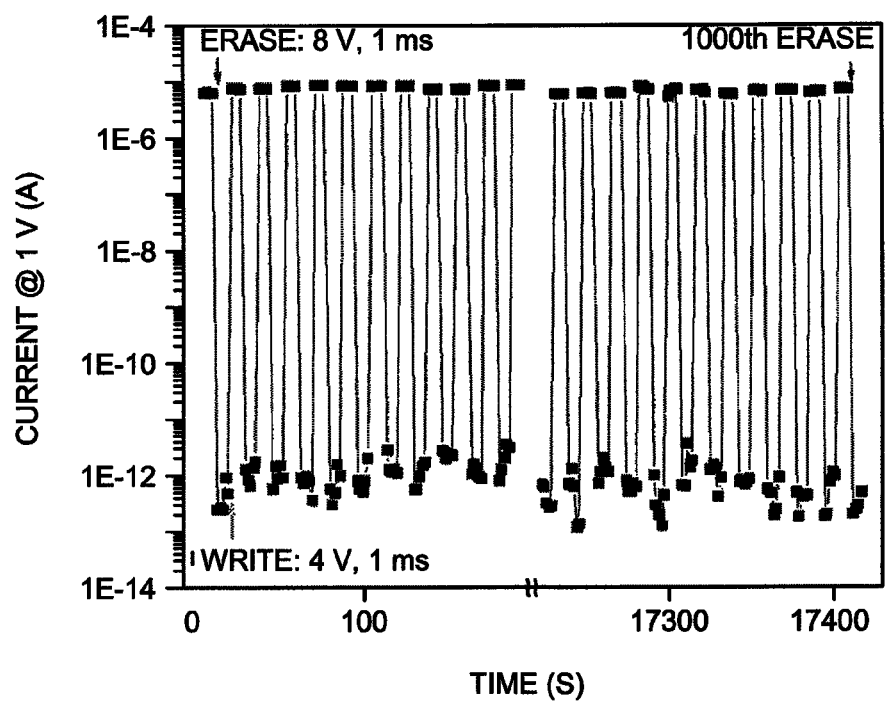
FIG. 30 shows an embodiment of the memory reading performance of a C—SiO$_2$ nanocable electronic device having a channel length of 2.6 μm and a nanocable diameter of 140 nm, as conducted with a +4 V write bias pulse for 1 ms and a +8 V erase bias pulse for 1 ms, each write/erase operation being followed by reading 5 consecutive times at +1 V.

FIG. 29 presents the BIV read/write performance of another C—SiO$_2$ nanocable device having a channel length of 2.6 μm and a nanocable diameter of 140 nm. The bistable memory switching performance of this device is shown in FIG. 30. As shown in FIG. 30, a pulse of +4 V for 1 ms turns the device to the high conduction ON state, and a pulse of +8 V for 1 ms returns the device to the low conduction OFF state. After each write/erase operation, the device was read consecutively at +1 V five times. After 1000 cycles of write-read and erase-read operations, there was no degradation in the ON/OFF current readings. The average ON/OFF ratio was 7.9×10$^6$.

Figure 31:
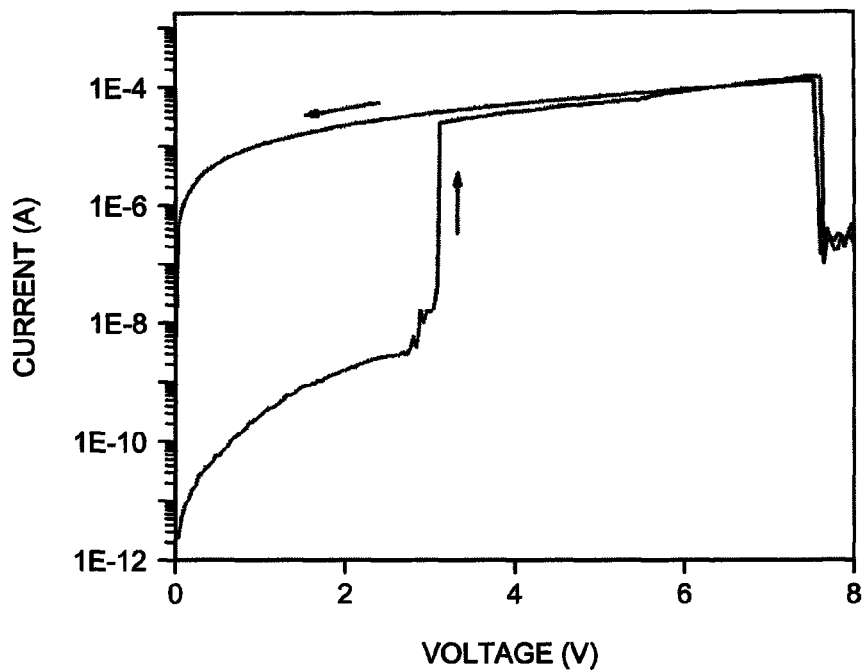
FIG. 31 shows an embodiment of a one-cycle read/write bias sweep sequence from 0 to +8 V for a C—SiO$_2$ nanocable electronic device having a channel length of 1.5 μm and a nanocable diameter of 200 nm.
Figure 32:
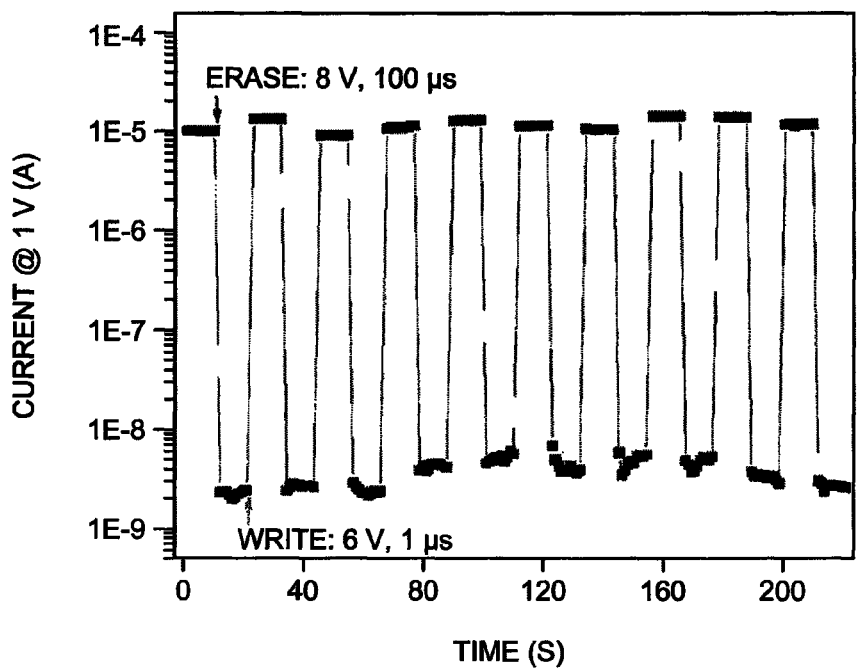
FIG. 32 shows an embodiment of the memory reading performance of a C—SiO$_2$ nanocable electronic device having a channel length of 1.5 μm and a nanocable diameter of 200 nm, as conducted with a +6 V write bias pulse for 1 μs and a +8 V erase bias pulse for 100 μs, each write/erase operation being followed by reading 10 consecutive times at +1 V.

FIG. 31 presents the BIV behavior of another C—SiO$_2$ nanocable device having a channel length of 1.5 μm and a nanocable diameter of 200 nm. The bistable memory switching performance of this device is shown in FIG. 32. As shown in FIG. 32, a pulse of +6 V for 1 μs is turns the device to the high conduction ON state, and a pulse of +8 V for 100 μs returns the device to the low conduction OFF state. After each write/erase operation, the device was read consecutively at +1 V ten times. The average ON/OFF ratio was 3.1×10$^3$. Although most the data presented herein for nanocable electronic devices is for 1 ms bias pulses, the data presented in FIG. 32 indicates that the devices can operate much faster. At shorter pulse times, however, a decrease in ON/OFF ratio was observed, and an increasing OFF current resulted. The ON current was relatively invariant under the pulse conditions, which suggests that writing may be performed using shorter pulses than erasing.

Without being limited by theory or mechanism, the results presented hereinabove for C—$SiO_2$—SiC, C—$SiO_2$—Si, and C—$SiO_2$ nanocable electronic devices collectively indicate that the outer graphene/graphite layer predominantly influences the BIV properties of the electronic devices. Control of the BIV properties may be influenced by a phase or structure change of the outer graphene/graphite layer as discussed in more detail hereinbelow.

Example 4

Figure 33:
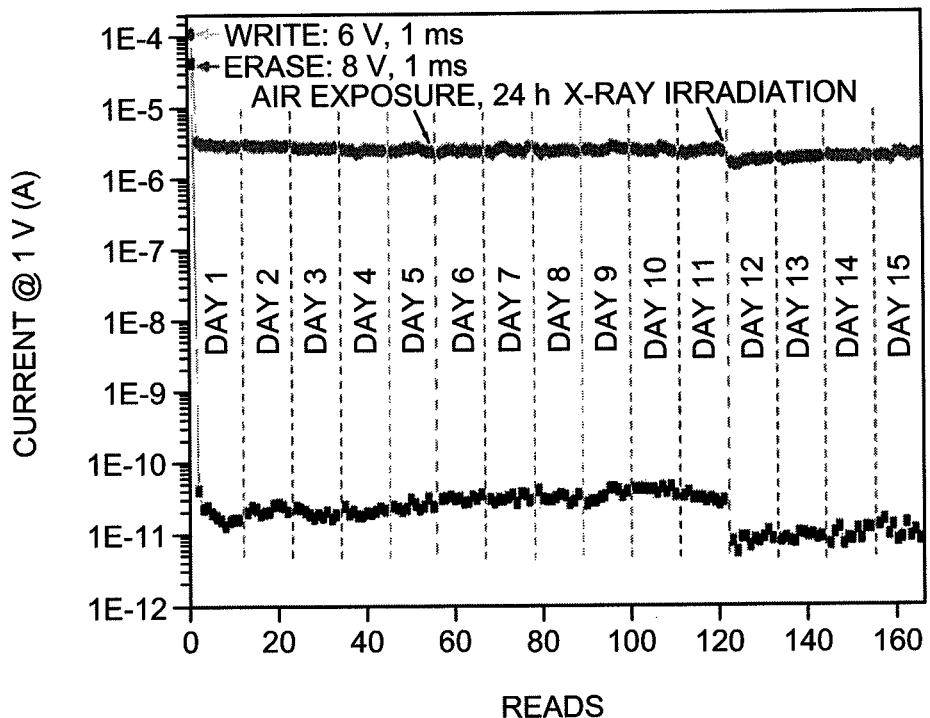
FIG. 33 shows an embodiment of the memory reading performance of two C—SiO$_2$ nanocable electronic devices, set to either the ON or OFF state prior to testing, over two weeks of testing time and exposure to different conditions.
Figure 34:
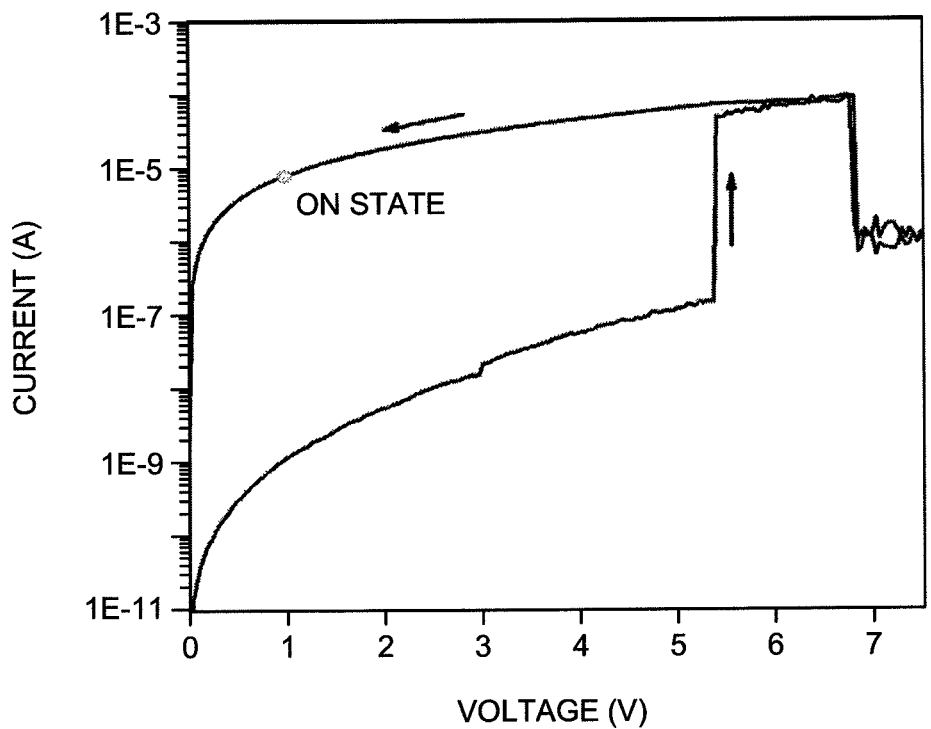
FIG. 34 shows an embodiment of the BIV behavior for a first C—SiO$_2$ nanocable device whose memory performance is shown in FIG. 33, prior to exposure to different testing conditions.
Figure 35:
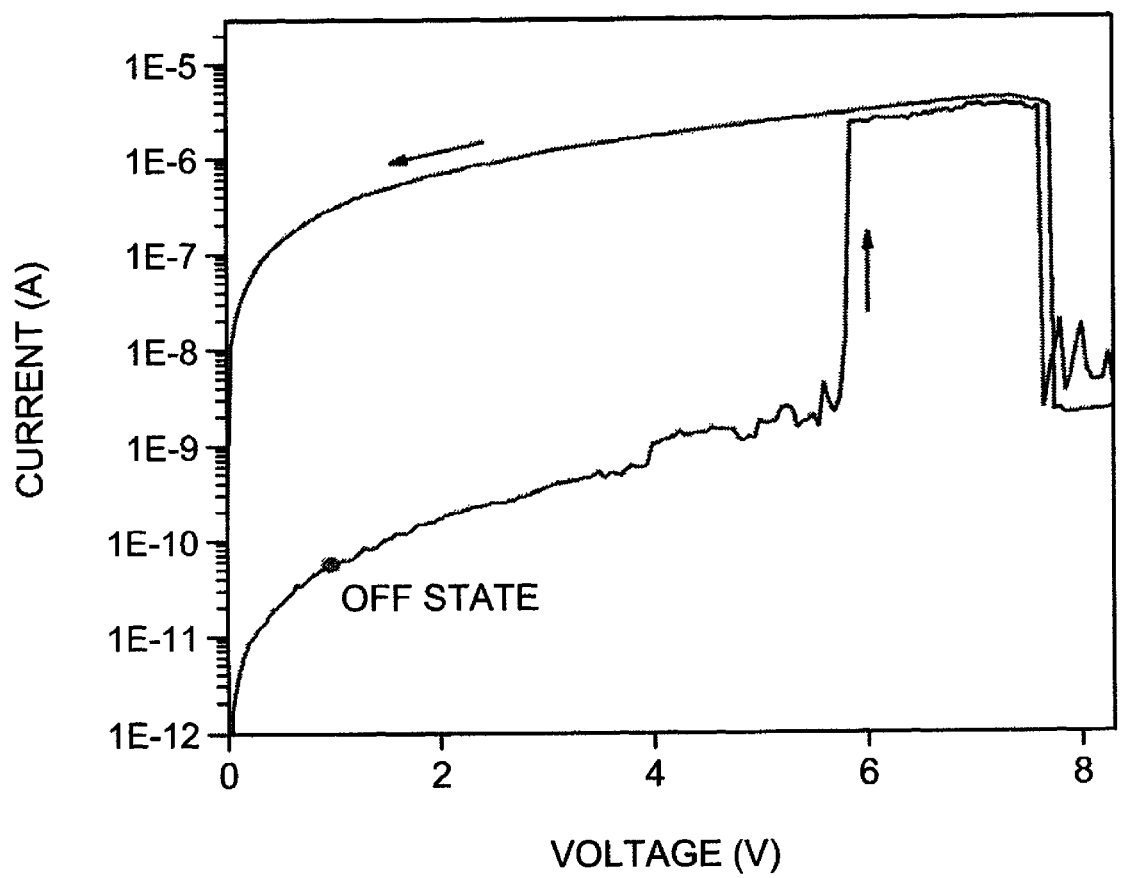
FIG. 35 shows an embodiment of the BIV behavior for a second C—SiO$_2$ nanocable device whose memory performance is shown in FIG. 33, prior to exposure to different testing conditions.
Figure 36A:
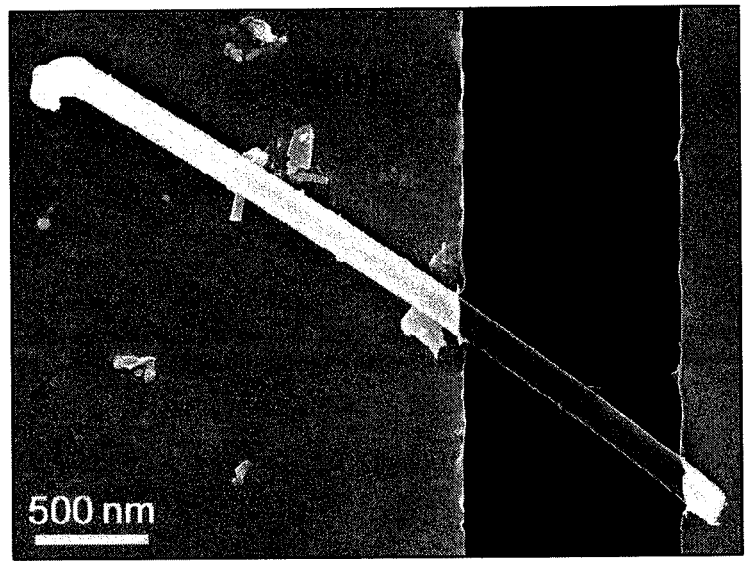
FIG. 36 shows embodiments of SEM images of C—SiO$_2$ nanocable electronic devices before and after the extended electrical property measurements presented in FIG. 33. The high magnification inset is denoted by an arrow.
Figure 36B:
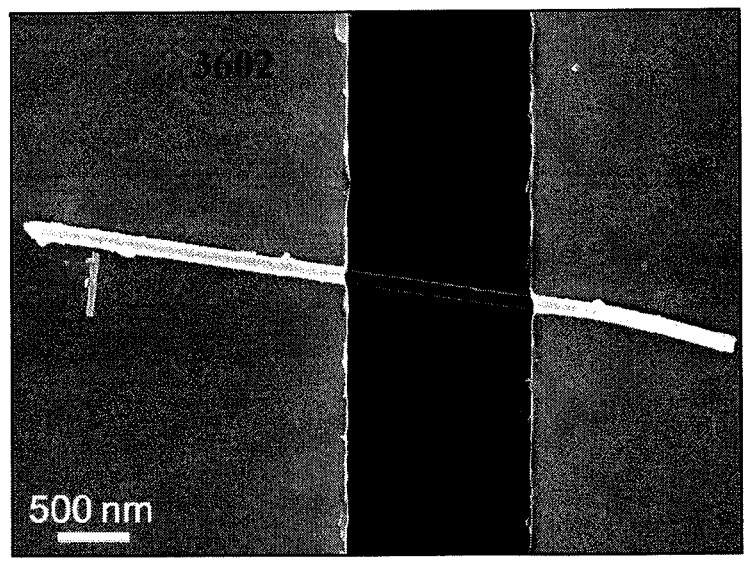
Figure 36C:
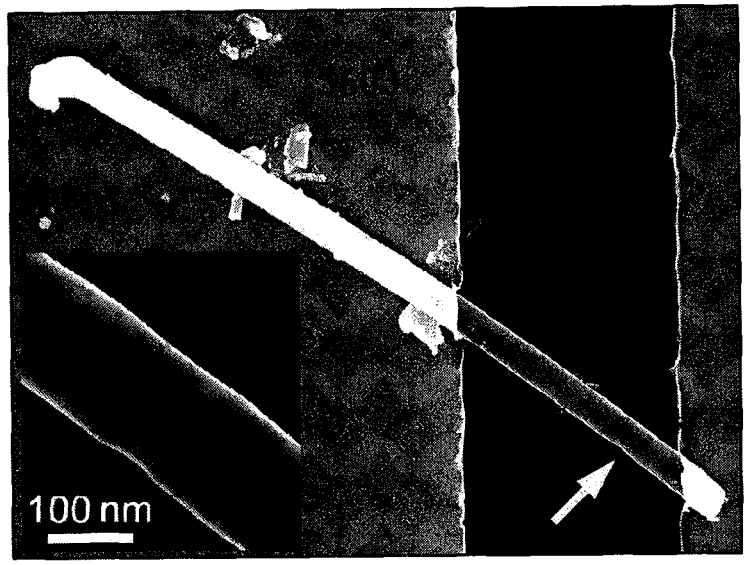
Figure 36D:
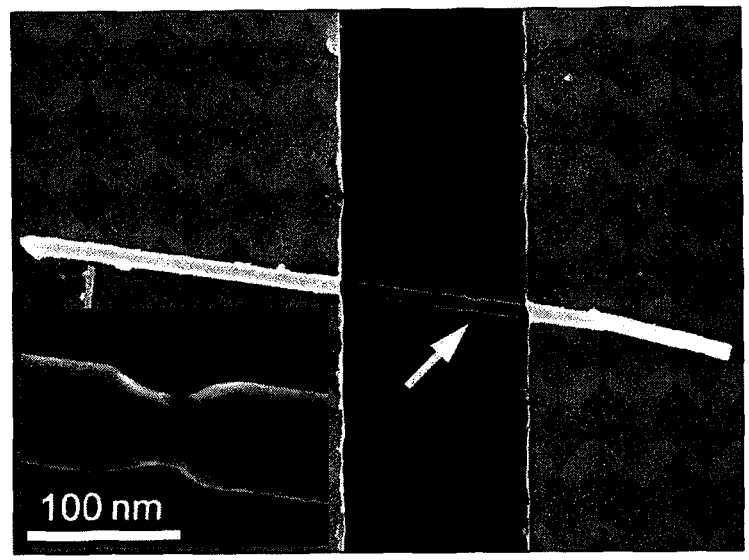

Performance of C—$SiO_2$ Nanocable Electronic Devices Under Different Testing Conditions Two C—$SiO_2$ nanocable devices were subjected to extended testing under conditions other than the typical high vacuum sample storage environment. FIG. 33 presents data obtained for two of the devices under these different testing conditions. BIV behaviors of these two devices before exposure to these different testing conditions are presented in FIGS. 34 and 35. As shown in FIG. 33, one device was set to the OFF state with a +8 V pulse for 1 ms, and the other device was set to the ON state by a +6 V pulse for 1 ms. The device currents were then read consecutively every day at +1 V ten times. Some of the testing was performed at 200° C. (data not shown), and there was no degradation in the devices or their memory retention properties. After five days, both devices were exposed to ambient air for 24 hours and then returned to high vacuum conditions for testing. After eleven days, both devices were irradiated with 1 Grad(Si) of X-rays and returned to high vacuum conditions for testing. As shown in FIG. 34, none of the extreme exposure conditions had significant effect on either the ON or OFF currents. The level of radiation exposure provided to the samples is higher than that of the typical failure rate of conventional memory devices relying on charge storage, such as flash memories. Thus, the nanocable electronic devices disclosed herein provide advantageous radiation stability.

FIG. 36 shows SEM images of the C—$SiO_2$ nanocable devices presented in FIG. 33 both before and after electrical property measurements presented hereinabove. Pre-testing image 3601 is for the C—$SiO_2$ nanocable device set to the OFF state in FIG. 33. Pre-testing image 3602 is for the C—$SiO_2$ nanocable device set to the ON state in FIG. 33. Post-testing image 3603 is for the C—$SiO_2$ nanocable device set to the OFF state in FIG. 33. Post-testing image 3604 is for the C—$SiO_2$ nanocable device set to the ON state in FIG. 33. The regions of inset in images 3603 and 3604 are denoted by arrows in the respective images. Images 3603 and 3604 show a defect site following testing.

Example 5

Figure 37A:
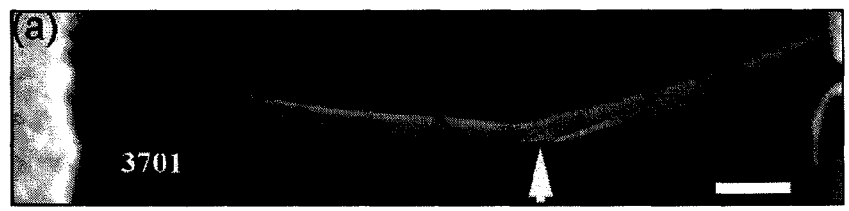
FIG. 37 shows embodiments of SEM images of multi-wall carbon nanotube (MWCNT) electronic devices, both before and after electrical breakdown.
Figure 37B:
Figure 38A:
FIG. 38 shows embodiments of SEM images of C—SiO$_2$ nanocable electronic devices, where graphite comprises the nanocable, both before and after electrical breakdown.
Figure 38B:

Investigation of Defect Sites with Respect to BIV Behavior in C—$SiO_2$ Nanocable Electronic Devices Two-terminal electronic devices with CVD-synthesized MWCNTs comprising the devices were prepared to compare their electrical behavior to that of C—$SiO_2$ nanocable electronic devices. FIG. 37 shows the SEM images of a two-terminal MWCNT-based electronic device as prepared (image 3701) and after electrical breakdown (image 3702). As can be seen in FIG. 37, electric breakdown occurred at a defect site. Recovery of conduction was not attainable for the MWCNT-based device. Similar defect site electrical breakdown occurred on the outer graphitic layer of a C—$SiO_2$ nanocable device similar to those presented hereinabove. As shown in FIG. 38, the diameter of G-$SiO_2$ nanocable thinned at the indicated section (image 3802) as compared to pre-breakdown image 3801. Characteristic breakdown-related features were found in all nanocables displaying BIV behavior, following application of a voltage bias. In contrast, devices for which no BIV behavior was observed did not produce notable differences between the SEM or AFM images recorded before and after electrical property measurements.

Not being limited by theory or mechanism, the current understanding of BIV behavior of nanocable devices based on graphene or graphite (G-based nanocable devices) results from voltage-induced breakdown damage at defect areas in the graphene or graphite shells. Switching of a nanoelectromechanical (NEM) nature at these sites is proposed. In MWCNT-based electronic devices, separated parts likely move apart after electrical breakdown, forming gaps of up to 20 nm in length, which are unlikely to restore conductance in the proposed mechanism. In contrast, in G-based nanocable devices, broken graphenic or graphitic sheets may remain very close to each other since they stick to the solid nanocable core. This allows for their rejoining under the electrostatic attraction when an axial electric field is applied. Thus, a relay-like voltage-induced opening/closing, accompanied with the erase/write operation, results in the BIV behavior of nanocables. A schematic of the proposed switching mechanism based on current mechanistic understanding is depicted in FIG. 39 where a weakest-defect section or sections are responsible for the switching. In FIG. 39, as synthesized graphenic or graphitic sheet 3901 is opened after application of a bias voltage to produce open defect 3902. The open defect 3903 is closed during writing and returned to open defect 3904 after erasing. In the proposed NEM mechanism presented here, motion of individual graphenic or graphitic sheets is on a near-atomic scale, and the switching thus resembles what is typically considered a filamentary effect.

Example 6

Temperature Dependent Current-Voltage Behavior of C—$SiO_2$ Nanocable Electronic Devices The proposed NEM switching mechanism of C—$SiO_2$ nanocable electronic devices comprising graphite or graphene is further supported by temperature dependent current-voltage studies. As shown in FIG. 40, the BIV switching of a C—$SiO_2$ nanocable electronic device comprising graphite fluctuated about 1 V in the ON and OFF voltages over the temperature range 250-400 K. At about 200 K, the switching behavior changed. The BIV characteristics of the C—$SiO_2$ nanocable device remained unchanged during the forward bias sweep from 0 to 10 V, but it remained in its low-conduction state during a reverse bias sweeping from 10 V to 0. The temperature dependence of graphitic sheet switching at low temperature again suggests a NEM effect.

Example 7

Memory Performance of Two-Terminal Electronic Devices

Figure 41A:
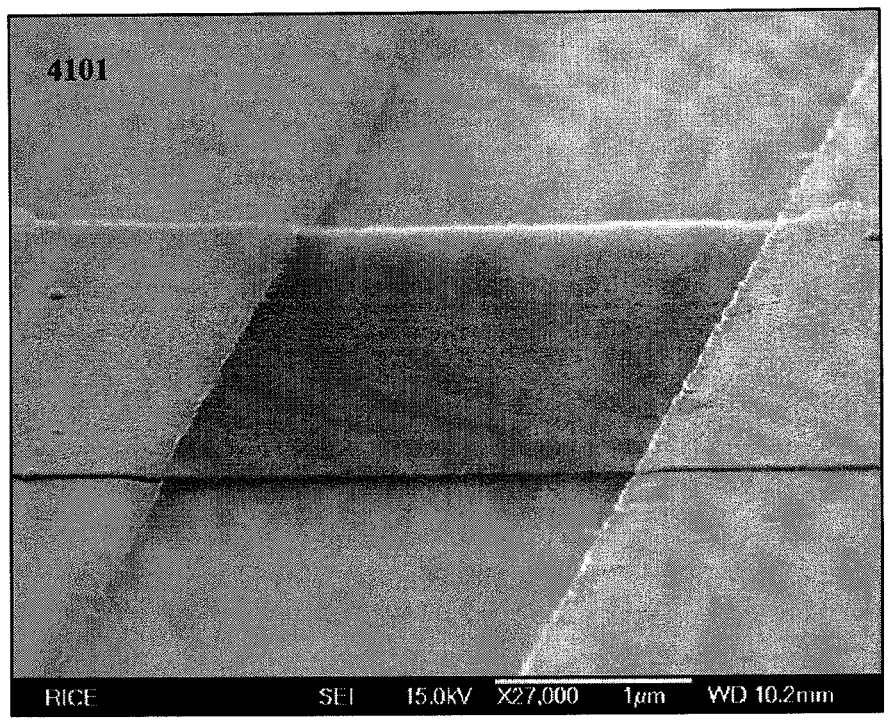
FIG. 41 shows embodiments of SEM images of a two-terminal electronic device fabricated according to FIG. 4, both before and after electrical breakdown.
Figure 41B:
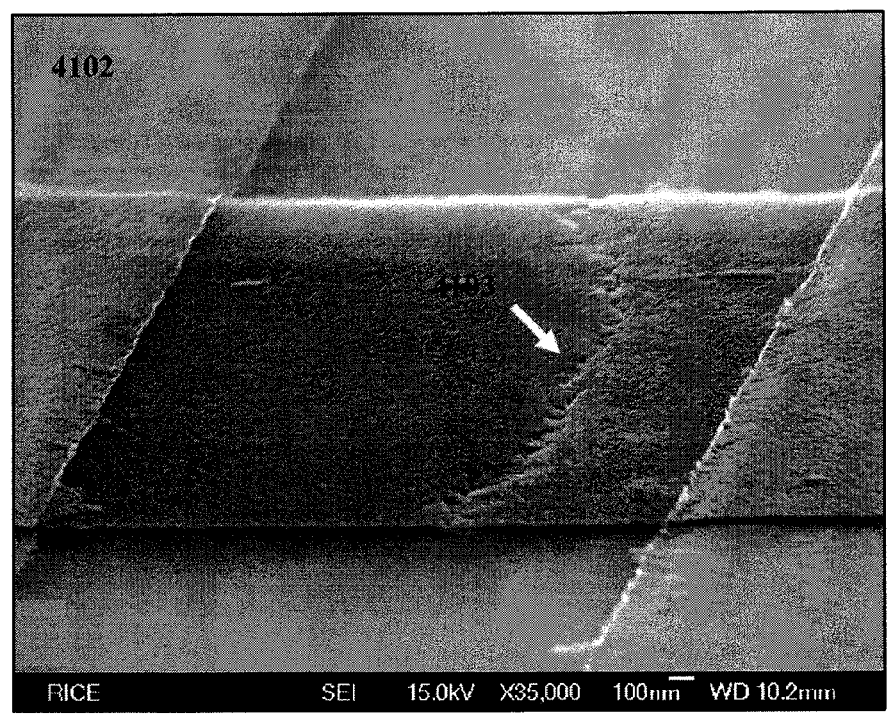

A two-terminal electronic device having a carbon layer was fabricated according to the general procedure outlined hereinabove and demonstrated previously in FIG. 4. The two-terminal electronic device exhibited BIV properties, which were similar to those observed for C—$SiO_2$, C—$SiO_2$—Si and C—$SiO_2$—SiC nanocable devices previously described hereinabove. FIG. 41 shows SEM images of the two-terminal electronic device both before (pre-testing image 4101) and after (post-testing image 4102) electrical breakdown. The breakdown damage region 4103 in image 4102 is denoted by an arrow. Changes in the appearance of two-terminal electronic device observed after electrical property measurements were similar to the changes in the appearance of nanocable devices observed after electrical property measurements shown in FIG. 36 and FIG. 37.

Figure 42:
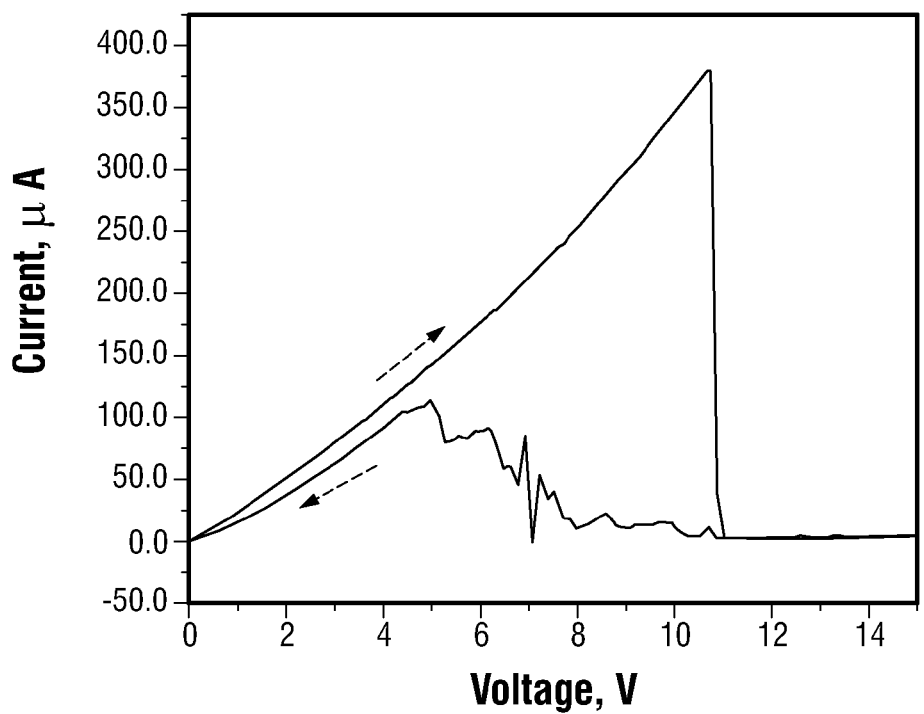
FIG. 42 shows an embodiment of BIV behavior over a bias sweep range of 0 V to +15 V for the two-terminal electronic device presented in FIG. 41 having a channel length of 2 width of 2 μm and carbon sheet thickness of 20 nm.
Figure 43:
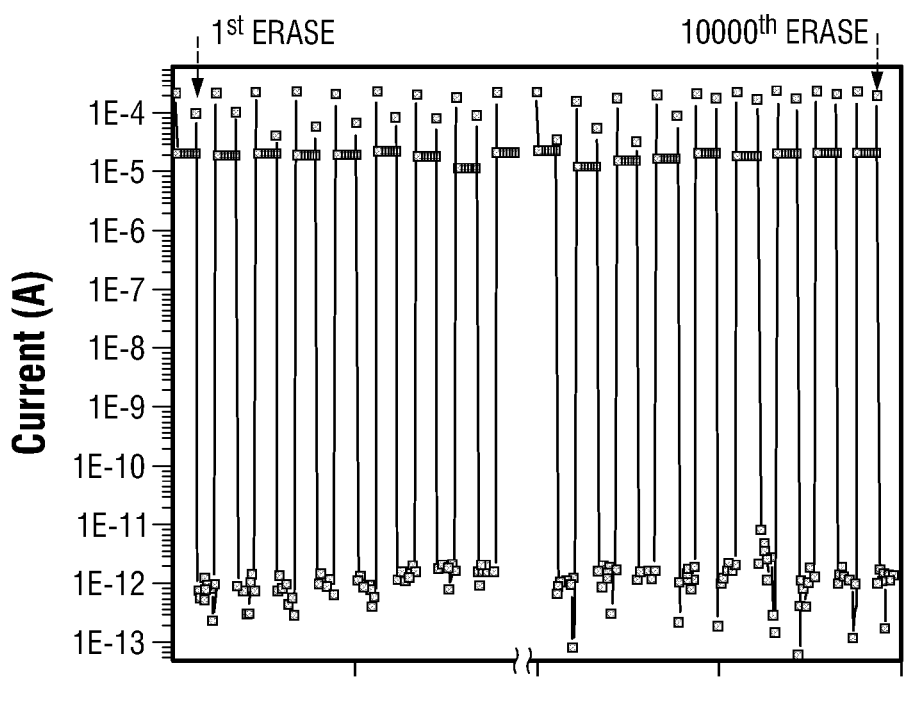
FIG. 43 shows an embodiment of the memory reading performance for the two-terminal electronic device presented in FIG. 42 over 10000 write/erase cycles, as conducted with a +8 V write bias pulse for 1 μs and a +15 V erase bias pulse for 1 μs.

As shown in FIG. 42, a two-terminal carbon layer electronic device having a channel length of 2 μm, a width of 2 μm and a carbon layer thickness of 20 nm showed typical BIV characteristics. The positive bias $V_{th}$ was +10.9 V. The bistable memory switching performance of this device is shown in FIG. 43. As shown in FIG. 43, a pulse of +8 V for 1 μs turned the device to the high conduction ON state, and a pulse of +15 V for 1 μs returned the device to the low conduction OFF state. After each write/erase operation, the device was read consecutively at +1 V 10 times. After 10000 cycles of write-read and erase-read operations, there was no degradation in the ON/OFF current readings. The average ON/OFF ratio was $9.3 \times 10^6$.

From the foregoing description, one skilled in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

What is claimed is the following:

1. An electronic device comprising:
    a dielectric material;
    two electrode terminals, wherein a first of the two electrode terminals comprises a source and a second of the two electrode terminals comprises a drain;
    at least two independent carbon sheets forming a discontinuous carbon layer disposed between the two electrode terminals, wherein the discontinuous carbon layer is deposited on the dielectric material, said at least two independent carbon sheets are selected from a group consisting of graphene, graphite, and combinations thereof, and the electronic device exhibits a nonlinear current-versus-voltage response when operated over a voltage sweep range; and
    a channel length between the two electrode terminals, wherein the channel length is less than 1 μm, and the nonlinear current-versus-voltage response comprises at least about a 10-fold change in current over a voltage sweep range of about 0.5 V.

2. The electronic device of claim 1, wherein the dielectric material is selected from a group consisting of silicon dioxide, silicon nitride, glass, and plastic.

3. The electronic device of claim 1 further comprising:
    a semiconductor; and
    wherein the dielectric material maintains continuous contact with the semiconductor.

4. The electronic device of claim 3, wherein the semiconductor is selected from a group consisting of silicon, silicon carbide, gallium arsenide, and germanium.

5. The electronic device of claim 3, wherein the semiconductor comprises a stacked silicon-on-insulator structure.

6. The electronic device of claim 3 further comprising:
    a gate electrode distinct from the source and the drain; and
    wherein the gate electrode influences performance of the semiconductor.

7. The electronic device of claim 1, wherein the at least one carbon sheet is deposited at a temperature between about 400° C. and about 900° C.

8. The electronic device of claim 7, wherein the at least one carbon sheet is deposited at a temperature between about 800° C. and about 900° C.

9. The electronic device of claim 1, wherein the at least one carbon sheet is deposited from a gas comprising at least one carbon-containing compound.

10. The electronic device of claim 9, wherein the at least one carbon-containing compound is selected from a group consisting of acetylene, ethylene, methane, ethane, carbon monoxide, and combinations thereof.

11. The electronic device of claim 9, wherein the gas further comprises hydrogen.

12. The electronic device of claim 1, wherein the at least one carbon sheet is deposited by a process selected from a group consisting of ink-jet printing and solution-spin coating.

13. The electronic device of claim 12, wherein the at least one carbon sheet is comprises a material selected from a group consisting of graphene, graphite, and combinations thereof.

14. The electronic device of claim 1, wherein the source and the drain are constructed from at least one material selected from a group consisting of platinum, palladium, gold, silver, silicon, gallium arsenide, titanium, tin, copper, and combinations thereof; and
    the selections of the at least one material for the source and for the drain are conducted independently.

15. The electronic device of claim 1, wherein the nonlinear current-versus-voltage response comprises a change in current between about 10-fold and $10^9$-fold over a voltage sweep range of about 0.5 V.

16. The electronic device of claim 15, wherein the nonlinear current-versus-voltage response comprises a change in current between about $10^5$-fold and $10^9$-fold over a voltage sweep range of about 0.5 V.

17. The electronic device of claim 1, wherein the electronic device is operated over a voltage sweep range of less than about 15 V.

18. The electronic device of claim 17, wherein the electronic device is operated over a voltage sweep range of less than about 5 V.

19. The electronic device of claim 18, wherein the electronic device is operated over a voltage sweep range of less than about 1 V.

20. The electronic device of claim 1, wherein the electronic device comprises a two-terminal memory device having an ON/OFF memory state.

21. The electronic device of claim 20, wherein the ON/OFF memory state has an ON/OFF ratio of at least about 10:1 for measuring recorded currents in the ON and OFF states.

22. The electronic device of claim 1 further comprising:
    a gate electrode above the at least one carbon sheet; and
    wherein the gate electrode modifies current flow through the at least one carbon sheet.

23. The electronic device of claim 1 further comprising:
    a gate electrode below the at least one carbon sheet; and
    wherein the gate electrode modifies current flow through the at least one carbon sheet.

24. The electronic device of any one of claim 1, 22 or 23 wherein the electronic device comprises a logic switch.

25. The electronic device of claim 1, wherein the electronic device is constructed on a planar silicon wafer.

26. The electronic device of claim 1 further comprising:
at least one nanowire; and
wherein the at least one nanowire lies between the source and the drain.

27. The electronic device of claim 1, wherein the dielectric material and the carbon sheets form a nanocable, wherein the nanocable comprises at least two layers of material.

28. The electronic device of claim 1, wherein the electronic device comprises a sensor.

29. The electronic device of claim 1 or claim 28, wherein the at least one carbon sheet is chemically functionalized with covalent bonds.

30. The electronic device of claim 29, wherein the covalent bonds connect the at least one carbon sheet to at least one moiety chosen from a group consisting of alkyls, arenes, saccharides, peptides, nucleotides, halides, and combinations thereof.

31. The electronic device of claim 29, wherein operation of the electronic device within the voltage sweep range promotes formation of the covalent bonds.

32. The electronic device of claim 1 or claim 28, wherein the at least one carbon sheet is modified through non-covalent bonding.

33. The electronic device of claim 32, wherein the non-covalent bonding comprises adsorption of at least one moiety to the at least one carbon sheet; and
wherein the at least one moiety is chosen from a group consisting of alkyls, arenes, saccharides, peptides, nucleotides, halides, styrenes, and combinations thereof.

34. The electronic device of claim 32, wherein operation of the electronic device within the voltage sweep range promotes modification through the non-covalent bonding.

35. The electronic device of claim 1 or claim 28, wherein operation of the electronic device within the voltage sweep range promotes displacement of at least one molecule from the at least one carbon sheet.

36. The electronic device of claim 35, wherein the at least one molecule comprises at least one analyte.

37. An analytical method comprising:
providing the electronic device of claim 1;
operating the electronic device over a voltage sweep range;
wherein the operating step occurs in the presence of at least one analyte; and
observing current-versus-voltage performance of the electronic device in the presence of the at least one analyte.

38. The analytical method of claim 37, wherein the at least one analyte becomes bound to the at least one carbon sheet during the operating step.

39. The analytical method of claim 38 further comprising:
removing the at least one analyte from the at least one carbon sheet after the operating step.

40. The analytical method of claim 37 further comprising:
comparing current-versus-voltage performance of the electronic device in the absence of the at least one analyte to the current-versus-voltage performance in the presence of the at least one analyte.

41. An electronic device prepared by a process comprising:
providing a dielectric material;
depositing at least two independent carbon sheets on the dielectric material, wherein said at least two independent carbon sheets are selected from a group consisting of graphene, graphite, and combinations thereof;
wherein the at least two independent carbon sheets form a discontinuous carbon layer; and
positioning two electrode terminals on the dielectric material;
wherein the at least two independent carbon sheets lie between the two electrode terminals to form a channel, and a channel length between the two electrode terminals is less than 1 μm;
wherein the electronic device provides a nonlinear current-versus-voltage response comprises at least about a 10-fold change in current over a voltage sweep range of about 0.5 V; and
wherein a first of the two electrode terminals comprises a source and a second of the two electrode terminals comprises a drain.

42. The electronic device prepared by the process of claim 41 further comprising:
applying a voltage sweep between the two electrode terminals; and
wherein the voltage sweep produces a nonlinear current-versus-voltage response.

43. The electronic device prepared by the process of claim 41, wherein the at least one carbon sheet is selected from a group consisting of graphene and graphite.

44. The electronic device prepared by the process of claim 41, wherein the dielectric material is selected from a group consisting of silicon dioxide, silicon nitride, glass, and plastic.

45. The electronic device prepared by the process of claim 41, wherein the dielectric material maintains continuous contact with a semiconductor.

46. The electronic device prepared by the process of claim 45, wherein the semiconductor is selected from a group consisting of silicon, silicon carbide, gallium arsenide, and germanium.

47. The electronic device prepared by the process of claim 45, wherein performance of the semiconductor is influenced by a gate electrode; and
wherein the gate electrode is distinct from the source and the drain.

48. The electronic device prepared by the process of claim 41, wherein the depositing step is performed with a gas comprising at least one carbon-containing compound.

49. The electronic device prepared by the process of claim 41, wherein the depositing step is performed by ink-jet printing.

50. The electronic device prepared by the process of claim 41, wherein the depositing step is performed by solution-spin coating.

51. The electronic device prepared by the process of claim 41, wherein the source and the drain are constructed from at least one material selected from a group consisting of platinum, palladium, gold, silver, silicon, gallium arsenide, titanium, tin, copper, and combinations thereof; and
the selections of the at least one material for the source and for the drain are conducted independently.

52. The electronic device prepared by the process of claim 41, wherein the nonlinear current-versus-voltage response comprises a change in current between about 10-fold and $10^9$-fold over a voltage sweep range of about 0.5 V.

53. The electronic device prepared by the process of claim 52, wherein the nonlinear current-versus-voltage response comprises a change in current between about $10^5$-fold and $10^9$-fold over a voltage sweep range of about 0.5 V.

54. The electronic device prepared by the process of claim 41 further comprising:
placing a gate electrode above the at least one carbon sheet; and wherein the gate electrode modifies current flow through the at least one carbon sheet.

55. The electronic device prepared by the process of claim 41 further comprising:
placing a gate electrode below the at least one carbon sheet; and
wherein the gate electrode modifies current flow through the at least one carbon sheet.

56. The electronic device prepared by the process of claim 41 further comprising:
chemically functionalizing the at least one carbon sheet with covalent bonds.

57. The electronic device prepared by the process of claim 41 further comprising:
chemically modifying the at least one carbon sheet with non-covalent bonds.

58. The electronic device prepared by the process of claim 41, wherein the at least one carbon sheet is formed in situ on the dielectric material.

* * * * *

UNITED STATES PATENT AND TRADEMARK OFFICE
CERTIFICATE OF CORRECTION

PATENT NO. : 8,440,467 B2  
APPLICATION NO. : 12/240673  
DATED : May 14, 2013  
INVENTOR(S) : James M. Tour, Yubao Li and Alexander Sinitskiy Page 1 of 1

It is certified that error appears in the above-identified patent and that said Letters Patent is hereby corrected as shown below:

Title page, Item (60), under Related U.S. Application Data, add "Provisional application No. 60/982,329, filed on Oct. 24, 2007"

Signed and Sealed this  
Second Day of July, 2013

Teresa Stanek Rea  
*Acting Director of the United States Patent and Trademark Office*